US011185481B2

(12) United States Patent
Lim et al.

(10) Patent No.: US 11,185,481 B2
(45) Date of Patent: Nov. 30, 2021

(54) USE OF EXOSOMES TO PROMOTE OR ENHANCE HAIR GROWTH

(71) Applicant: **AGENCY FOR SCIENCE, TECHNOLOGY AND RESEARCH (A*STAR)**, Singapore (SG)

(72) Inventors: Sai Kiang Lim, Singapore (SG); Mathew Sze Wei Yeo, Singapore (SG); Tian Sheng Chen, Singapore (SG); Ruenn Chai Lai, Singapore (SG)

(73) Assignee: **AGENCY FOR SCIENCE, TECHNOLOGY AND RESEARCH (A*STAR)**, Singapore (SG)

( * ) Notice: Subject to any disclaimer, the term of this patent is extended or adjusted under 35 U.S.C. 154(b) by 37 days.

(21) Appl. No.: 15/224,844

(22) Filed: Aug. 1, 2016

(65) Prior Publication Data

US 2017/0135915 A1    May 18, 2017

Related U.S. Application Data

(63) Continuation of application No. 14/444,113, filed on Jul. 28, 2014, now abandoned, which is a continuation of application No. 13/879,905, filed as application No. PCT/SG2011/000362 on Oct. 17, 2011, now abandoned.

(30) Foreign Application Priority Data

Oct. 18, 2010 (SG) ................ 201007660-2

(51) Int. Cl.
| | | |
|---|---|---|
| A61K 8/14 | (2006.01) | |
| A61P 17/02 | (2006.01) | |
| A61K 8/98 | (2006.01) | |
| A61K 35/28 | (2015.01) | |
| A61K 9/00 | (2006.01) | |
| A61Q 7/00 | (2006.01) | |
| A61P 17/14 | (2006.01) | |
| A61K 38/17 | (2006.01) | |
| A61K 38/02 | (2006.01) | |

(52) U.S. Cl.
CPC ............ *A61K 8/14* (2013.01); *A61K 8/981* (2013.01); *A61K 9/0014* (2013.01); *A61K 9/0019* (2013.01); *A61K 35/28* (2013.01); *A61K 38/02* (2013.01); *A61K 38/1709* (2013.01); *A61P 17/02* (2018.01); *A61P 17/14* (2018.01); *A61Q 7/00* (2013.01); *A61K 2800/413* (2013.01); *A61K 2800/86* (2013.01)

(58) Field of Classification Search
None
See application file for complete search history.

(56) References Cited

U.S. PATENT DOCUMENTS

| | | | |
|---|---|---|---|
| 2006/0088505 A1 | 4/2006 | Hoffmann et al. | |
| 2006/0116321 A1 | 6/2006 | Robbins et al. | |
| 2006/0165667 A1* | 7/2006 | Laughlin | A61K 35/28 424/93.21 |
| 2007/0292401 A1* | 12/2007 | Harmon | A61K 35/28 424/93.21 |

FOREIGN PATENT DOCUMENTS

| | | | |
|---|---|---|---|
| WO | 2008/036374 A2 | 3/2008 | |
| WO | 2008/103471 | 8/2008 | |
| WO | 2009/105044 | 8/2009 | |
| WO | WO-2009105044 A1 * | 8/2009 | ............ A61K 35/12 |
| WO | 2010/038232 A1 | 4/2010 | |
| WO | 2011/010966 A1 | 1/2011 | |

OTHER PUBLICATIONS

Nishio et al. "Neutrophil depletion delays wound repair in aged mice", Age 30: 11-19, 2008 (Year: 2008).*
Yoon et al. "Secretory profiles and wound healing effects of human amniotic fluid-derived mesenchymal stem cells." Stem Cells and Development 19.6 (2010): 887-902. (Year: 2010).*
Kong et al., Clinical and Experimental Pharmacology and Physiology, 37(4):e136-e144 (2010). "Germ plasm-like Dot cells maintain the wound regenerative function after in vitro expansion." Abstracts 589-594, Journal of Investigative Dermatology (2009).
Baer et al., "Mesenchymal stem cell interactions with growth factors on kidney repair", Curr Opin Nephrol Hypertens 19, 1-6 (2010).
Caplan et al., "Mesenchymal stem cells as trophic mediators", Journal of Cellular Biochemistry 98:1076-1084 (2006).
Cha et al., "Stem cells in cutaneous wound healing", Clin Dermatol 25, 73-78 (2007).
Fu et al., "Enhanced wound-healing quality with bone marrow mesenchymal stem cells autografting after skin injury" Wound Repair Regen 14:325-335 (2006).
Granero et al.,Role of mesenchymal stem cells in regenerative medicine: application to bone and cartilage repair. Expert Opin Biol Ther 8:255-268. (2008).
Kim et al., "Protective role of adipose-derived stem cells and their soluble factors in photoaging", Arch Dermatol Res 301:329-336 (2009).
Kim et al., Wound healing effect of adipose-derived stem cells: a critical role of secretory factors on human dermal fibroblasts. J Dermatol Sci 48:15-24 (2007).
Lai et al., "Derivation and characterization of human fetal MSCs: An alternative cell source for large-scale production of cardioprotective microparticles", J Mol Cell Cardiol. 48:1215-1224 (2010).
Li et al., "Adult bone-marrow-derived mesenchymal stem cells contribute to wound healing of skin appendages", Cell Tissue Res, 326:725-736 (2006).

(Continued)

*Primary Examiner* — Emily A Cordas
(74) *Attorney, Agent, or Firm* — Nixon Peabody LLP; Mark J. Fitzgerald

(57) ABSTRACT

We describe the use of an exosome for the preparation of a pharmaceutical composition to promote or enhance would healing or hair growth, or both, in an individual. The exosome may be derived from a stem cell such as a mesenchymal stem cell (MSC).

9 Claims, 5 Drawing Sheets

(56) References Cited

OTHER PUBLICATIONS

Sadan et al., "Bone-marrow-derived mesenchymal stem cell therapy for neurodegenerative diseases", Expert Opin. Biol. Ther. 9(12):1487-1497 (2009).

Spitkovsky, D. and Hescheler, J., "Adult mesenchymal stromal stem cell for therapeutic applications", Minimally Invasive Therapy 17(2):79-90 (2008).

Thery et al., "Membrane vesicles as conveyors of immune responses", Nat Rev Immunol 9:581-593 (2009).

Wu et al., "Bone marrow-derived stem cells in wound healing: a review", Wound Repair Regen 15(Suppl 1):S18-26 (2007b).

Yoon et al., "Secretory Profiles and Wound Healing Effects of Human Amniotic Fluid-derived Mesenchymal Stem Cells", Stem Cells Dev. 19(6):887-902 (2009).

Nishio et al., "Neutrophil depletion elays wound repair in aged mice", Age 30: 11-19 (2008).

Raposo et al., "Extracellular vesicles: exosomes, microvesicles, and friends", J. of Cell Biology 200(4):373-83 (2013).

Bruno et al., "Mesenchymal stem cell-derived microvesicles protect against acute tubular injury", J. of the Amer. Soc. of Nephr., 20(5): 1053-67 (2009).

Abdallah et al., "The use of mesenchymal skeletal) stem cells for treatment of degenerative diseases: current status and future perspectives", Journal of Cellular Physiology pp. 9-12 (2008).

Arthur et al. "The Therapeutic applications of multipotential mesenchymal stromal stem cells in skeletal tissue repair", Journal of Cellular Physiology, 218:237-245 (2009).

Chen et al., "Paracrine factors of mesenchymal stem cells recruit macrophages and endothelial lineage cells and enhance wound healing", PLOS One 3(4):e1886 (2008).

Chen et al., "Mesenchymal stem cell secrets microparticles enriched in pre-microRNAs", Nucleic Acids Research 38 (1):215-224 (2010).

Cowan et al., "Derivation of embryonic stem cells from human blastocyst", The New England Journal of Medicine 350(13):1353-1356 (2004).

Giordano et al., "From the laboratory bench to the patient's bedside an update on clinical trials with mesenchymal stem cells", Journal of Cellular Physiology 211:27-35 (2007).

Lai et al., "Exosome secreted by MSC reduces myocardial ischemia/ reperfusion injury", Stem Cell Research 4:214-222 (2010).

Lian et al., "Derivation of clinically compliant MSCs from CD105+, CD24– differentiated human ESCs", Stem Cells 25:425-436 (2007).

Phinney et al., "Concise Review: Mesenchymal stem/ multipotent stromal cells: the state of transdifferentiation and modes of tissue repair—current views", Stem Cells 25:2896-2902 (2007).

Sasaki et al., "Mesenchymal stem cells are recruited into wounded skin and contribute to wound repair by transdifferentiation in to multiple skin cell type", J. Immunol 180:2581-2587 (2008).

Sze et al., "Elucidating the secretion proteome of human embryonic stem cell-derived mesenchymal stem cells", Molecular Cellular Proteomics 6.10 pp. 1680-1689 (2007).

Thomson et al., "Embryonic stem cells lines from human blastocyst", Science 28:1145-1147 (1998).

Timmers et al., "Reduction of myocardial infarct size by human mesenchymal stem cell conditioned medium", Stem Cell Research 1:129-137 (2008).

Wu et al., "mesenchymal stem cell enhance wound healing through differentiation and angiogenesis", Stem Cells 25:2648-2659 (2007).

Escamez et al., "An in vivo model of wound helaing in genetically modified skin-humanized mice." The Journal of Investigative Dermatology 123(6): 1182-1191 (2004).

FDA, "Guidance for Industry: Chronic Cutaneous Ulcer and Burn Wounds—Developing Products for Treatment" (2006).

Shevchenko et al., "A review of tissue-engineered skin bioconstructs avilable for skin reconstruction." J. Royal Soc. Interface 7: 229-258 (2009).

Sivamani et al., "Wound re-epithelialization: modulating keratinocyte migration in wound healing." Frontiers in Bioscience 12: 2849-2868 (2007).

\* cited by examiner

USE OF EXOSOMES TO PROMOTE OR ENHANCE HAIR GROWTH

CROSS REFERENCE TO RELATED APPLICATIONS

This application is a continuation application of U.S. patent application Ser. No. 14/444,113 filed Jul. 28, 2014, which is a continuation application of U.S. patent application Ser. No. 13/879,905 filed Apr. 17, 2013, which is a 35 U.S.C. § 371 National Phase Entry Application of International Application No. PCT/SG2011/000362 filed Oct. 17, 2011, which designates the U.S., and which claims benefit of Singapore Patent Application No. 201007660-2 filed Oct. 18, 2010, the contents of each of which are incorporated herein by reference in their entireties.

FIELD

The present invention relates to the fields of medicine, cell biology, molecular biology and genetics. This invention also relates to the field of cosmetics and medicine.

BACKGROUND

Androgenic alopecia (also known as androgenetic alopecia or alopecia androgenetica) is the most common cause of hair loss in humans. Variants appear in both men and women. It also occurs in chimpanzees, and orangutans.

In humans, this condition is also commonly known as male pattern baldness. In classic pattern baldness, hair is lost in a well-defined pattern, beginning above both temples. Hair also thins at the crown of the head. Often a rim of hair around the sides and rear of the head is left. This type of pattern is dubbed "Hippocratic balding" and may rarely progress to complete baldness. Women do not suffer classic male pattern baldness, instead the hair becomes thinner around the whole scalp, and the hairline does not recede. This is dubbed "female pattern baldness" and may occur in males. This variety of androgenic alopecia in women rarely leads to total baldness.

A variety of genetic (and possibly environmental) factors apparently play a role in androgenic alopecia. Although researchers have long studied the factors that may contribute to this condition, many remain unknown. Minimally, pattern hair loss is related to hormones called androgens, particularly dihydrotestosterone (DHT). Androgens are important for normal male sexual development before birth and during puberty. Androgens also have other important functions in both males and females, such as regulating hair growth and sex drive.

Male pattern baldness is caused by a genetic sensitivity of hair follicles to DHT. This hormone causes follicles to shrink or "miniaturize". In turn, this shortens their lifespan and prevents them from producing hair normally.

Recently the existing theories have been challenged on the ground that while the androgens in question are responsible for hair growth on the face and all over the body of men, hair loss only occurs at the top of the scalp. For example, it has been suggested that androgenic alopecia is a consequence of the anabolic effect of androgens such as hormonal changes leading to structural changes in skin and scalp which in turn cause hair loss.

Treatment of alopecia ranges from camouflage measures, such as hairpieces and wigs, colouring the scalp to disguise thinning, and cosmetic thickening products to give the illusion of greater hair volumes, through to medical intervention, such as hair transplants and treatment with drugs. The U.S. Food and Drug Administration (FDA) has approved only two medications for the treatment of male pattern baldness; minoxidil (ROGAINE®) and finasteride (PROPECIA®).

Minoxidil (ROGAINE®) is a vasodilator originally used as an oral drug (LONITEN™) to treat high blood pressure. However, minoxidil was discovered to have the side effect of hair growth and reversing baldness. Consequently, in the 1980s, Upjohn Corporation received FDA approval to market a topical solution that contained 2% minoxidil to be used to treat baldness and hair loss as ROGAINE®, marketed as REGAINE® outside the USA.

Objective evidence shows that minoxidil is effective for treatment of male-pattern hair loss in both the frontal areas and the vertex area of the scalp. At the conclusion of a 48 week study, improvements were seen in the vertex area regions of 51% of men using 5% minoxidil, 42% using 2% minoxidil, and 13% of placebo users. Among these men, moderate to great increases in hair growth were seen in the frontal scalp regions of 19% of men using 5% minoxidil, 10% using 2% minoxidil, and 3% of placebo users.

The mechanism of action for minoxidil is not known. Its action as a vasodialator may involve opening vascular smooth muscle potassium channels or "K-channels", perhaps through mimicking the most important natural vasodialator, nitric oxide, whose structure minoxidil incorporates. This agent can also cause follicles in the telogen phase to shed, usually soon to be replaced by new, thicker hairs. As the hair-growth-stimulating effect is temporary and does not seem to change the follicle in any other way, minoxidil needs to be applied regularly (once or twice daily) for hair gained to be maintained. Side effects with minoxidil include pruritus and contact allergic dermatitis.

Finasteride (marketed by Merck under the trade names PROPECIA® and PROSCAR®) is a 5 alpha-reductase inhibitor of the type II isoenzyme. Finasteride is recommended as first-line treatment for male pattern baldness. They may also be used simultaneously when hair loss is progressive or further regrowth is desired after 12 months.

It was originally FDA approved for treatment of benign prostatic hyperplasia (BPH) and works by binding to 5-alpha-reductase, the enzyme responsible for the conversion of free testosterone to DHT.

In 1997, finasteride was approved by the US FDA for the treatment of male pattern baldness. A 5-year study revealed that 9 of 10 men taking finasteride (1 mg/day) experienced visible results (42% of men taking Propecia experienced no further hair loss while 48% experienced no further hair loss and hair regrowth). In clinical studies, finasteride, like minoxidil, was shown to work on both the crown area and the hairline area, but is most successful in the crown area. Side effects of finasteride include lowered male libido and erectile dysfunction. Trials in women show only limited success of finasteride in slowing hair loss, and it is a teratogen, posing a risk to the unborn child.

None of these hair loss compositions have been found to be entirely satisfactory. Given the high prevalence of premature hair loss and the psychological impact it has on sufferers, there exists a need for a more effective hair loss treatment that contains natural or naturally-derived compounds which may provide a safer alternative to the treatments currently available, and which retain usability and suitable aesthetic properties.

SUMMARY

Surprisingly, it has been found that a composition comprising exosomes may be used to promote or enhance hair growth. This is demonstrated in the Examples. The Examples also show that such a composition can also aid wound healing.

According to a 1$^{st}$ aspect of the present invention, we provide for the use of an exosome for the preparation of a pharmaceutical composition to promote or enhance hair growth.

The pharmaceutical composition may further enhance would healing.

The pharmaceutical composition may promote or enhance human wound healing or human hair growth, or both.

The exosome may be derived from a stem cell. The stem cell may comprise a mesenchymal stem cell (MSC).

The percentage of a group of test animals, for example C57BL/6J female mice, to which the pharmaceutical composition is applied which show growth of thick, straight hair may be 50% or higher. It may be 55% or higher, such as 60% or higher, such as 65% or higher, such as 70% or higher, such as 75% or higher.

The percentage of a group of control animals to which the pharmaceutical composition is not applied which show growth of thick, straight hair may be 40% or lower, such as 35% or lower, such as 30% or lower, such as 25% or lower, such as 20% or lower, such as 15% or lower.

The time taken for a wound to completely heal (complete wound closure) in a test animal to which the pharmaceutical composition is applied may be 90% or shorter than the time taken for complete wound closure in a control animal on which the pharmaceutical composition is not applied. The time taken may be 85% or shorter, 80% or shorter, 75% or shorter, 70% or shorter, 65% or shorter or 50% or shorter.

The mean time taken for complete wound healing in a group of test animals to which the pharmaceutical composition is applied may be 90% or shorter than the mean time taken for complete wound closure in a control group of animals on which the pharmaceutical composition is not applied. The mean time taken may be 85% or shorter, 80% or shorter, 75% or shorter, 70% or shorter, 65% or shorter or 50% or shorter.

The mean time for complete wound healing in a group of test animals may be 14.6 days or 13 days. The mean time for complete wound healing in a group of control animals may be 17 days, or both.

The test animal or group of test animals may comprise(s) a C57BL/6J female mouse. The wound may comprise a biopsy punch of 177 mm$^2$ (15-mm diameter wound).

An amount of pharmaceutical composition containing 10 μg or less, such as 5 μg or less, such as 2 μg or less, such as 1 μg or less, such as 0.5 μg or less, such as 0.3 μg of exosome may be applied to the test animal.

The pharmaceutical composition may comprise 40 μg/ml or less, 20 μg/ml or less, 8 μg/ml or less, 4 μg/ml or less, 2 μg/ml or less or 1.2 μg/ml or less of exosome.

The pharmaceutical composition may be subcutaneously injected or applied topically.

The exosome may have a size of between 50 nm and 100 nm as determined by electron microscopy.

The exosome may comprise a complex of molecular weight>100 kDa, for example comprising proteins of <100 kDa.

The exosome may comprise a complex of molecular weight>300 kDa, for example comprising proteins of <300 kDa.

The exosome may comprise a complex of molecular weight>1000 kDa.

The exosome may have a size of between 2 nm and 200 nm, such as a size of between 50 nm and 150 nm or a size of between 50 nm and 100 nm, for example as determined by filtration against a 0.204 filter and concentration against a membrane with a molecular weight cut-off of 10 kDa.

The exosome may have a hydrodynamic radius of below 100 nm, such as between about 30 nm and about 70 nm, between about 40 nm and about 60 nm, such as between about 45 nm and about 55 nm, such as about 50 nm, for example as determined by laser diffraction or dynamic light scattering.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

DETAILED DESCRIPTION

Figures 1A, 1B:
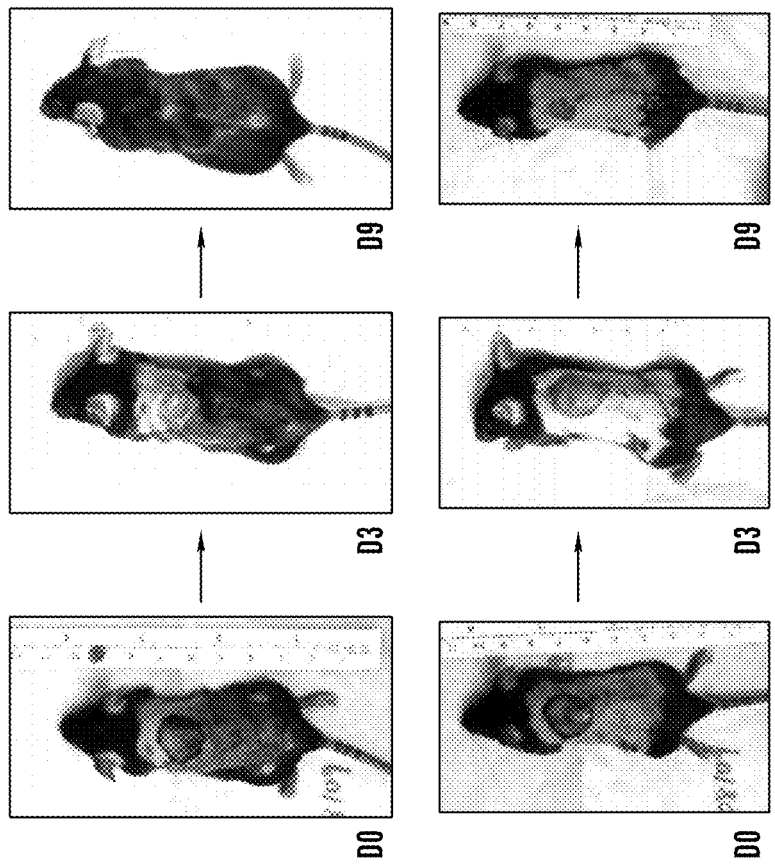
FIGS. 1A-1B are diagrams showing a representative mouse treated with either exosome (1A) or saline (1B) at day 0 (D0), day 3 (D3) and day 9 (D9).

This invention is based on the surprising discovery that exosomes derived from and secreted by stem cells such as mesenchymal stem cells are capable of promoting or enhancing hair growth. Such exosomes are capable of promoting wound healing.

We therefore describe a composition for the treatment or prevention of hair loss and/or the promotion of hair regrowth comprising an exosome and optionally a dermatologically acceptable carrier.

We also describe a method for the treatment or prevention of hair loss and/or the promotion of hair regrowth, which method comprises the application to the skin of a composition as described above.

Most commonly, the area of the skin to which the composition is applied will be the scalp, i.e., the composition will be used to combat hair loss on the user's head. Other areas may be suitable for application, for example to promote the growth of eyebrow hair, or eyelashes.

In addition to treating or preventing hair loss and/or promoting the growth of the hair, the methods and compositions described here may also improve the appearance of hairs to which the composition is applied, eg by thickening the hair and improving the lustre, condition and manageability of the hair.

We further describe an article of manufacture containing a topical dosage form prepared from exosomes, packaged for retail distribution, in association with instructions advising the consumer how to use the product to promote hair growth.

Hair Growth

Exosomes as described here may be used in the preparation of dosage forms to promote hair growth, as desired by the user, or to prevent a decrease in hair growth in a subject (including optionally of promoting wound healing).

Thus, the exosomes may be used to manufacture formulations containing exosomes. Typically, the formulation will be suitable for topical administration to a mammal. More typically, it will be used to promote hair growth. Such formulations will generally be applied directly to the scalp, especially to those areas in which hair is absent, or thinning. The dose will vary, but as a general guideline, the exosomes will be present in a dermatological formulation comprising a dermatologically acceptable carrier in an amount of from 0.01 to 10 w/w %, and the dermatological formulation will be applied to the area to be treated from 1 to 4 times daily. More typically, the exosomes will be present in a quantity of from 1 to 3 w/w %, and the exosomes will be applied once or twice daily.

The formulations may also be used to treat patients who have not yet experienced hair loss, but believe that they are at risk of doing so. Examples of such patients include those who will be undergoing cancer chemotherapy with a drug regimen known to induce alopecia.

Young adults experiencing mental distress at the thought of balding, especially those with a family history of baldness, may also benefit from such prophylactic treatment. Such prophylactic treatment is encompassed by the term "promoting hair growth".

"Promoting hair growth" includes stimulating an increase in total hair mass and/or length. Such increase includes increased length and/or growth rate of hair shafts (i.e. follicles), increased number of hairs, and/or increased hair thickness.

Methods of assessing promotion of hair growth are known in the art and are described below and in the Examples.

A straightforward method for assessing improvement in hair growth is by taking a photograph of a test area of the skin before and after application of exosome composition. The skin may optionally be shaved for this purpose. A photograph is taken. The treatment is then applied. A second photograph is then taken. The increase in hair growth may be quantified by counting any combination of: (a) number of hairs appearing; (b) length of hair appearing; (c) thickness of hair appearing; (d) straightness of hair appearing; (e) area of hair growth. Where the skin is not shaved, the relevant measurements may be with regard to improvement in the measured parameters, i.e., number of new hairs, increase in length of hair, increase in thickness of hair, increase in straightness of hair and increase in area of hair growth.

For example, hair growth may be assessed in an individual. An individual to whom the pharmaceutical composition is administered may display enhanced hair growth, as measured by any of the parameters described above, of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100% or more. This may be compared to hair growth in an individual to which the pharmaceutical composition is not administered. The enhanced hair growth may be assessed by number of additional or thick or straight hairs. It may be assessed by an increased area of hair growth.

As a further example, a group of test animals may be assessed to identify individuals which have thick, straight hair. Such test animals may include any suitable animals, such as C57BL/6J female mice. The percentage of a group of test animals, for example C57BL/6J female mice, to which the pharmaceutical composition is applied which show growth of thick, straight hair may be 50% or higher, such as 55% or higher, such as 60% or higher, such as 65% or higher, such as 70% or higher, such as 75% or higher, such as 80% or higher, such as 85% or higher, such as 90% or higher, such as 95% or higher, such as 100% or higher.

Where a group of test animals is employed, the percentage of test animals which do not display thick, straight hair in the non-treatment group may also be assessed. The percentage of a group of control animals to which the pharmaceutical composition is not applied which show growth of thick, straight hair may be 40% or lower, such as 35% or lower, such as 30% or lower, such as 25% or lower, such as 20% or lower, such as 15% or lower, such as 10% or lower, such as 5% or lower, such as 2% or lower, such as 1% or lower.

Some or all of the above improvements can be achieved by prolonging or activating anagen, the growth phase of the hair cycle, or by shortening or delaying the catagen and telogen phases Hair growth results from a dynamic cyclic process of hair follicles and many common disorders of hair growth relate to alterations in the timing of the hair growth cycle. The hair growth cycle includes a growth phase (anagen), a transition phase (catagen) and a resting phase (telogen). During healthy hair growth situations, over 90% of scalp hair follicles are in anagen, 7% to 9% are in telogen and 1% to 3% are in catagen.

Anagen is the growth phase, during which the follicle (i.e. the hair root) penetrates deep into the dermis with the cells of the follicle dividing rapidly and differentiating. During the differentiation process, the hair cells synthesize keratin, the predominant component of hair. In non-balding humans, this growth phase lasts from one to five years.

Catagen is the transitional phase and is marked by the cessation of mitosis. Catagen generally lasts from about two to three weeks.

Telogen is the resting phase in which the hair is retained within the scalp for up to 12 weeks, until it is displaced by new follicular growth from the scalp below.

In humans, this growth cycle is not synchronized. An individual will have thousands of follicles in each of these three phases. However, most of the hair follicles will be in the anagen phase. In healthy young adults, the anagen to telogen ratio can be as high as 9 to 1. In individuals with alopecia, this ratio is reduced to as low as 2:1.

The most common form of hair loss is androgenic alopecia, a hereditary decrease of cosmetically useful hair induced by androgens in genetically predisposed men and women. This condition is also commonly referred to as male pattern baldness and female pattern baldness. While androgens are associated with some forms of balding, the physiological mechanism by which this hair loss occurs is not known. However, it is known that hair growth is altered in individuals afflicted with alopecia. The exosomes may be used to manufacture a product to promote hair growth in individuals suffering from this type of alopecia.

While the exosomes will most typically be used to alleviate androgenic alopecia, their uses are not limited to this specific condition. The exosomes may be used to alleviate any type of alopecia. Examples of non-androgenic alopecia include alopecia areata, alopecia due to radiotherapy or chemotherapy, scarring alopecia, stress related alopecia, etc. As used in this application, "alopecia" refers to partial or complete hair loss on the scalp, including, but not limited to sparse hair growth, short hair growth, thin hair growth, etc.

Thus, the exosomes can be applied topically to the scalp and hair to prevent, or alleviate balding. Further, the exosomes can be applied topically in order to induce or promote the growth of hair on the scalp.

Hair loss also occurs in a variety of in other conditions.

Anagen effluvium, is hair loss due to chemicals or radiation, such as chemotherapy or radiation treatment for cancer. It is also commonly referred to as "drug induced" or "radiation induced" alopecia. The exosomes may used be to manufacture preparations to treat these types of alopecia.

Alopecia areata is an autoimmune disorder which initially presents with hair loss in a rounded patch on the scalp. It can progress to the loss of all scalp hair, which is known as alopecia totalis and to the loss of all scalp and body hair, which is known as alopecia universalis. The exosomes may be used to manufacture preparations to treat these types of alopecia.

Traumatic alopecia is the result of injury to the hair follicle. It is also commonly referred to as "scarring alopecia". Psychogenic alopecia occurs due to acute emotional stress. By inducing anagen, the exosomes can be beneficial in these types of alopecia as well. Thus, the uses of the exosomes are not limited to treating androgenetic alopecia.

The exosomes can be used to manufacture preparations to alleviate any type of hair loss.

The exosomes may be used to manufacture preparations to promote hair growth in other mammals besides humans. For example, the exosomes may be used with farm animals such as sheep, in which fur (hair) growth would exhibit an economic benefit. The exosomes may also be used to stimulate hair growth in companion animals such as dogs, cats, gerbils, etc. The dosages required to obtain this effect will fit within the guidelines described above. Likewise, the exosomes may be administered using formulations typically used for veterinary applications, taking into account the type of animal being treated. Other applications of the exosomes to promote hair growth will become readily apparent to one skilled in the art based upon the disclosure of this application and should be considered to be encompassed by the claims.

As a general guideline, the preparations manufactured from exosomes will be administered topically. They will be applied directly to the areas of the skin requiring hair growth promotion. Such areas may include any suitable areas such as the scalp, eyebrows, eyelashes, etc.

"Eyebrow" as used in this document refers to an area of coarse skin hairs above the eye that follows the shape of the brow ridges. The main function of the eyebrow is to prevent moisture, mostly salty sweat and rain, from flowing into the eye, an organ critical to sight. The typical curved shape of the eyebrow (with a slant on the side) and the direction in which eyebrow hairs are pointed, make sure that moisture has a tendency to flow sideways around the eyes, along the side of the head and along the nose. Eyebrows also prevent debris such as dandruff and other small objects from falling into the eyes, as well as providing a more sensitive sense for detecting objects being near the eye, like small insects. Eyebrows also have an important facilitative function in communication, strengthening facial expressions such as surprise, confusion, or anger.

The terms "eyelash" and "lash" are used interchangeably to refer to one of the hairs that grow at the edge of the eyelid. Eyelashes protect the eye from debris and provide a warning that an object (such as an insect or dust mite) is near the eye (which then is closed reflexively).

Administration

The exosome composition may be applied to skin and hair using any suitable treatment regime.

The exosome composition may be applied at least once a week, such as at least every two days, or at least once each day. For example, application may be twice per day.

In general, treatment using the exosome composition described here may be continued indefinitely. Alternatively, the treatment may be repeated only for a limited period, e.g. several weeks or months. Treatment may then be repeated for a similar period at a later date.

After application to the skin, the composition may be rinsed off, or may be left on the skin (and hair). If the composition is to be rinsed off after application, the composition may be left on for a minimum period of time before rinsing. An example period of time is more than 30 seconds, such as more than 1 minute, such as more than 3 minutes.

The product may be massaged into the skin, most commonly into the scalp, during application, such as for at least 5 seconds, such as for at least 20 seconds.

Particularly beneficial results may be obtained by the use of two or more different forms of composition concurrently. For example, for the treatment or prevention of hair loss and/or the promotion of hair regrowth on the head, a user may wash their hair with a shampoo and then use a conditioner, both the shampoo and the conditioner constituting exosome compositions, the user massaging each product into their scalp before rinsing. The user may subsequently apply another form of exosome composition described here, eg a gel or lotion, directly to the scalp with gentle massage, that composition being left on the head until the user next washes their hair.

Exosomes

The exosome composition may be made from an exosome. The exosome may be derivable from a stem cell such as a mesenchymal stem cell (MSC), as described below and in WO 2009/105044.

The exosome may be derivable from a MSC by any of several means, for example by secretion, budding or dispersal from the MSC. For example, the exosome may be produced, exuded, emitted or shed from the MSC. Where the MSC is in cell culture, the exosome may be secreted into the cell culture medium.

The exosome may in particular comprise a vesicle.

The exosome may comprise vesicles or a flattened sphere limited by a lipid bilayer. The exosome may comprise diameters of 40-100 nm. The exosome may be formed by inward budding of the endosomal membrane. The exosome may have a density of ~1.13-1.19 g/ml and may float on sucrose gradients. The exosome may be enriched in cholesterol and sphingomyelin, and lipid raft markers such as GM1, GM3, flotillin and the src protein kinase Lyn. The exosome may comprise one or more proteins present in mesenchymal stem cells or mesenchymal stem cell conditioned medium (MSC-CM), such as a protein characteristic or specific to the MSC or MSC-CM. They may comprise RNA, for example miRNA.

We provide a exosome which comprises one or more genes or gene products found in MSCs or medium which is conditioned by culture of MSCs, for use in enhancing hair growth or promoting wound healing or both. The exosome may comprise molecules secreted by the MSC. Such an exosome, and combinations of any of the molecules comprised therein, including in particular proteins or polypeptides, may be used for any of the methods described in this document.

The exosome may comprise a cytosolic protein found in cytoskeleton e.g. tubulin, actin and actin-binding proteins, intracellular membrane fusions and transport e.g. annexins and rab proteins, signal transduction proteins e.g. protein kinases, 14-3-3 and heterotrimeric G proteins, metabolic enzymes e.g. peroxidases, pyruvate and lipid kinases, and enolase-1 and the family of tetraspanins e.g. CD9, CD63, CD81 and CD82. In particular, the exosome may comprise one or more tetraspanins. The exosomes may comprise mRNA and/or microRNA.

The exosome may be something that is isolatable from a mesenchymal stem cell (MSC) or mesenchymal stem cell conditioned medium (MSC-CM). The exosome may be responsible for at least an activity of the MSC or MSC-CM. The exosome may be responsible for, and carry out, substantially most or all of the functions of the MSC or MSC-CM. For example, the exosome may be a substitute (or biological substitute) for the MSC or MSC-CM.

The exosome preferably has at least one property of a mesenchymal stem cell. The exosome may have a biological property, such as a biological activity. The exosome may have any of the biological activities of an MSC. The exosome may for example have a therapeutic or restorative activity of an MSC.

The exosome may be isolated from a mesenchymal stem cell conditioned medium (MSC-CM).

Mesenchymal Stem Cell Conditioned Medium (MSC-CM)

The conditioned cell culture medium such as a Mesenchymal Stem Cell Conditioned Medium (MSC-CM) may be obtained by culturing a mesenchymal stem cell (MSC), a descendent thereof or a cell line derived therefrom in a cell culture medium; and isolating the cell culture medium. The mesenchymal stem cell may be produced by a process comprising obtaining a cell by dispersing a embryonic stem (ES) cell colony. The cell, or a descendent thereof, may be propagated in the absence of co-culture in a serum free medium comprising FGF2.

Mesenchymal Stem Cell Exosome

The exosome may be produced or isolated in a number of ways. Such a method may comprise isolating the exosome from a mesenchymal stem cell (MSC). Such a method may comprise isolating the exosome from an mesenchymal stem cell conditioned medium (MSC-CM).

The exosome may be isolated for example by being separated from non-associated components based on any property of the exosome. For example, the exosome may be isolated based on molecular weight, size, shape, composition or biological activity.

The conditioned medium may be filtered or concentrated or both during, prior to or subsequent to separation. For example, it may be filtered through a membrane, for example one with a size or molecular weight cut-off. It may be subject to tangential force filtration or ultrafiltration.

For example, filtration with a membrane of a suitable molecular weight or size cutoff, as described in the Assays for Molecular Weight elsewhere in this document, may be used.

The conditioned medium, optionally filtered or concentrated or both, may be subject to further separation means, such as column chromatography. For example, high performance liquid chromatography (HPLC) with various columns may be used. The columns may be size exclusion columns or binding columns.

One or more properties or biological activities of the exosome may be used to track its activity during fractionation of the mesenchymal stem cell conditioned medium (MSC-CM). As an example, light scattering, refractive index, dynamic light scattering or UV-visible detectors may be used to follow the exosome. For example, a therapeutic activity such as cardioprotective activity may be used to track the activity during fractionation.

The following paragraphs provide a specific example of how a mesenchymal stem cell exosome may be obtained.

A mesenchymal stem cell exosome may be produced by culturing mesenchymal stem cells in a medium to condition it. The mesenchymal stem cells may comprise HuES9.E1 cells. The medium may comprise DMEM. The DMEM may be such that it does not comprise phenol red. The medium may be supplemented with insulin, transferrin, or selenoprotein (ITS), or any combination thereof. It may comprise FGF2. It may comprise PDGF AB. The concentration of FGF2 may be about 5 ng/ml FGF2. The concentration of PDGF AB may be about 5 ng/ml. The medium may comprise glutamine-penicillin-streptomycin or □-mercaptoethanol, or any combination thereof.

The cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more.

The conditioned medium may be subject to liquid chromatography such as HPLC. The conditioned medium may be separated by size exclusion. Any size exclusion matrix such as SEPHAROSE® may be used. As an example, a TSK GAURD® column SWXL, 6×40 mm or a TSK GEL® G4000 SWXL, 7.8×300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector.

Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The $r_h$ of exosomes in this peak is about 45-55 nm. Such fractions comprise mesenchymal stem cell exosomes.

Exosome Molecular Weight

The exosome may have a molecular weight of greater than 100 kDa. It may have a molecular weight of greater than 500 kDa. For example, it may have a molecular weight of greater than 1000 kDa.

The molecular weight may be determined by various means. In principle, the molecular weight may be determined by size fractionation and filtration through a membrane with the relevant molecular weight cut-off. The exosome size may then be determined by tracking segregation of component proteins with SDS-PAGE or by a biological assay.

Assay of Molecular Weight by SDS-PAGE

The exosome may have a molecular weight of greater than 100 kDa. For example, the exosome may be such that most proteins of the exosome with less than 100 kDa molecular weight segregate into the greater than 100 kDa molecular weight retentate fraction, when subject to filtration. Similarly, when subjected to filtration with a membrane with a 500 kDa cut off, most proteins of the exosome with less than 500 kDa molecular weight may segregate into the greater than 500 kDa molecular weight retentate fraction. This indicates that the exosome may have a molecular weight of more than 500 kDa.

Assay of Molecular Weight by Biological Activity

The exosome may have a molecular weight of more than 1000 kDa. For example, the exosome may be such that when subject to filtration with a membrane with a molecular weight cutoff of 1000 kDa, the relevant biological activity substantially or predominantly remains in the retentate fraction. Alternatively or in addition, biological activity may be absent in the filtrate fraction. The biological activity may comprise any of the biological activities of the exosome described elsewhere in this document.

Assay of Molecular Weight by Infarct Size

For example, the biological activity may comprise reduction of infarct size, as assayed in any suitable model of myocardia ischemia and reperfusion injury. For example, the biological activity may be assayed in a mouse or pig model, as described in WO 2009/105044.

In summary, myocardial ischemia is induced by 30 minutes left coronary artery (LCA) occlusion by suture ligation and reperfusion is initiated by removal of suture. Mice are treated with liquid containing the exosomes (such as unfractionated MSC-CM), filtrate (such as <100 or 1,000 kD fraction), retentate (such as >1000 kD retentate) or saline intravenously via the tail vein, 5 minutes before reperfusion. 24 hours later, the hearts are excised. Before excision, the Area At Risk (AAR) is determined by religating the LCA and then perfusing Evans blue through the aorta.

AAR is defined as the area not stained by the dye and is expressed as a percentage of the left ventricular wall area. Infarct size is assessed 24 hours later using Evans blue and TTC. Where the relative infarct size is significantly reduced in animals treated with mesenchymal stem cell conditioned medium (MSC-CM) and the retentate (such as a >1000 kD) fraction when compared to saline, this indicates that the exosome has a molecular weight which is higher than the relevant cutoff of the membrane (e.g., greater than 1000 kDa).

Exosome Size

The exosome may have a size of greater than 2 nm. The exosome may have a size of greater than 5 nm, 10 nm, 20 nm, 30 nm, 40 nm or 50 nm. The exosome may have a size of greater than 100 nm, such as greater than 150 nm. The exosome may have a size of substantially 200 nm or greater.

The exosome may have a range of sizes, such as between 2 nm to 20 nm, 2 nm to 50 nm, 2 nm to 100 nm, 2 nm to 150 nm or 2 nm to 200 nm. The exosome may have a size between 20 nm to 50 nm, 20 nm to 100 nm, 20 nm to 150 nm or 20 nm to 200 nm. The exosome may have a size between 50 nm to 100 ηm, 50 ηm to 150 nm or 50 nm to 200 nm. The exosome may have a size between 100 nm to 150 nm or 100 nm to 200 nm. The exosome may have a size between 150 nm to 200 nm.

The size may be determined by various means. In principle, the size may be determined by size fractionation and filtration through a membrane with the relevant size cut-off. The exosome size may then be determined by tracking segregation of component proteins with SDS-PAGE or by a biological assay.

The size may also be determined by electron microscopy.

The size may comprise a hydrodynamic radius. The hydrodynamic radius of the exosome may be below 100 nm. It may be between about 30 nm and about 70 nm. The hydrodynamic radius may be between about 40 nm and about 60 nm, such as between about 45 nm and about 55 nm. The hydrodynamic radius may be about 50 nm.

The hydrodynamic radius of the exosome may be determined by any suitable means, for example, laser diffraction or dynamic light scattering. An example of a dynamic light scattering method to determine hydrodynamic radius is described in WO 2009/105044.

Exosome

Exosomes are small membrane vesicles formed in late endocytic compartments (multivesicular bodies) first described to be secreted by reticulocytes in 1983 and subsequently found to be secreted by many cells types including various haematopoietic cells, tumours of haematopoietic or non-haematopoietic origin and epithelial cells. They are distinct entities from the more recently described 'ribonuclease complex' also named exosome.

Exosomes may be defined by a number of morphological and biochemical parameters. Accordingly, the exosome described here may comprise one or more of these morphological or biochemical parameters.

Exosomes are classically defined as "saucer-like" vesicles or a flattened sphere limited by a lipid bilayer with diameters of 40-100 nm and are formed by inward budding of the endosomal membrane. Like all lipid vesicles and unlike protein aggregates or nucleosomal fragments that are released by apoptotic cells, exosomes have a density of ~1.13-1.19 g/ml and float on sucrose gradients. Exosomes are enriched in cholesterol and sphingomyelin, and lipid raft markers such as GM1, GM3, flotillin and the src protein kinase Lyn suggesting that their membranes are enriched in lipid rafts.

The molecular composition of exosomes from different cell types and of different species has been examined. In general, exosomes contain ubiquitous proteins that appear to be common to all exosomes and proteins that are cell-type specific. Also, proteins in exosomes from the same cell-type but of different species are highly conserved. The ubiquitous exosome-associated proteins include cytosolic proteins found in cytoskeleton e.g. tubulin, actin and actin-binding proteins, intracellular membrane fusions and transport e.g. annexins and rab proteins, signal transduction proteins e.g. protein kinases, 14-3-3 and heterotrimeric G proteins, metabolic enzymes e.g. peroxidases, pyruvate and lipid kinases, and enolase-1 and the family of tetraspanins e.g. CD9, CD63, CD81 and CD82. The tetraspannins are highly enriched in exosomes and are known to be involved in the organization of large molecular complexes and membrane subdomains.

Examples of cell-type specific proteins in exosomes are MEW class II molecules in exosomes from MEW class II-expressing cells, CD86 in dendritic cell-derived exosomes, T-cell receptors on T-cell-derived exosomes etc. Notably, exosomes do not contain proteins of nuclear, mitochondrial, endoplasmic-reticulum or Golgi-apparatus origin. Also, highly abundant plasma membrane proteins are absent in exosomes suggesting that they are not simply fragments of the plasma membrane. Many of the reported ubiquitous exosome-associated proteins are also present in the proteomic profile of the hESC-MSC secretion.

Exosomes are also known to contain mRNA and microRNA, which can be delivered to another cell, and can be functional in this new location. The physiological functions of exosome remain poorly defined. It is thought to help eradicate obsolete proteins, recycle proteins, mediate tramission of infectious particles such as prions and viruses, induce complement resistance, facilitate immune cell-cell communication and transmit cell signaling. Exosomes have been used in immunotherapy for treatment of cancer.

Obtaining Mesenchymal Stem Cells (MSC)

The exosomes described here may be isolated or produced from mesenchymal stem cell conditioned medium (MSC-CM). MSCs suitable for use in the production of conditioned media and exosomes may be made by any method known in the art.

In particular, MSCs may be made by propagating a cell obtained by dispersing a embryonic stem (ES) cell colony, or a descendent thereof, in the absence of co-culture in a serum free medium comprising FGF2. This is described in detail in the sections below.

The prior art methods of obtaining mesenchymal stem cells (MSC) or MSC-like cells from hESCs involve either transfection of a human telomerase reverse transcriptase (hTERT) gene into differentiating hESCs (Xu et al., 2004) or coculture with mouse OP9 cell line (Barberi et al., 2005). The use of exogenous genetic material and mouse cells in these derivation protocols introduces unacceptable risks of tumorigenicity or infection of xenozootic infectious agents.

The exosomes may therefore be made from MSCs derived by the use of a clinically relevant and reproducible protocol for isolating similar or identical (such as homogenous) MSC populations from differentiating hESCs. In general, the method comprises dispersing a embryonic stem (ES) cell colony into cells. The cells are then plated out and propagated. The cells are propagated in the absence of co-culture in a serum free medium comprising fibroblast growth factor 2 (FGF2), in order to obtain mesenchymal stem cells (MSCs).

Thus, the protocol does not require serum, use of mouse cells or genetic manipulations and requires less manipulations and time, and is therefore highly scalable. The protocol may be used for the isolation of MSCs from two different hESC lines, HuES9 and H-1 and also a third one, Hes-3. Human ES cell derived MSCs (hESC-MSCs) obtained by the methods and compositions described here are remarkably similar to bone-marrow derived MSCs (BM-MSCs).

The embryonic stem cell culture may comprise a human embryonic stem cell (hESC) culture.

In a one embodiment, a method of generating mesenchymal stem cells (MSC) comprises trypsinizing and propagating hESCs without feeder support in media supplemented with FGF2 and optionally PDGF AB before sorting for CD105+CD24− cells.

The method may comprise sorting for CD105+, CD24− cells from trypsinized hESCs one week after feeder-free propagation in a media supplemented with FGF2 and optionally PDGF AB will generate to generate a hESC-MSC cell culture in which at least some, such as substantially all, or all cells are similar or identical (such as homogenous) to each other.

The MSCs produced by this method may be used to produce mesenchymal stem cell conditioned medium (MSC-CM), from which the exosomes may be isolated.

Disaggregating Embryonic Stem Cell Colonies

One method of producing mesenchymal stem cells may comprise dispersing or disaggregating an embryonic stem cell colony into cells.

The embryonic stem cell colony may comprise a huES9 colony (Cowan C A, Klimanskaya I, McMahon J, Atienza J, Witmyer J, et al. (2004) *Derivation of embryonic stem-cell lines from human blastocysts.* N Engl J Med 350: 1353-1356) or a H1 ESC colony (Thomson J A, Itskovitz-Eldor J, Shapiro S S, Waknitz M A, Swiergiel J J, et al. (1998) *Embryonic Stem Cell Lines Derived from Human Blastocysts.* Science 282: 1145-1147.).

The cells in the colony may be disaggregated or dispersed to a substantial extent, i.e., at least into clumps. The colony may be disaggregated or dispersed to the extent that all the cells in the colony are single, i.e., the colony is completely disaggregated.

The disaggregation may be achieved with a dispersing agent.

The dispersing agent may be anything that is capable of detaching at least some embryonic stem cells in a colony from each other. The dispersing agent may comprise a reagent which disrupts the adhesion between cells in a colony, or between cells and a substrate, or both. The dispersing agent may comprise a protease.

The dispersing agent may comprise trypsin. The treatment with trypsin may last for example for 3 minutes or thereabouts at 37 degrees C. The cells may then be neutralised, centrifuged and resuspended in medium before plating out.

The method may comprise dispersing a confluent plate of human embryonic stem cells with trypsin and plating the cells out.

The disaggregation may comprise at least some of the following sequence of steps: aspiration, rinsing, trypsinization, incubation, dislodging, quenching, re-seeding and aliquoting. The following protocol is adapted from the Hedrick Lab, UC San Diego (see the hypertext transfer protocol (http), hedricklab.ucsd.edu/Protocol/COSCell.html).

In the aspiration step, the media is aspirated or generally removed from the vessel, such as a flask. In the rinsing step, the cells are rinsed with a volume, for example 5-10 mls, of a buffered medium, which is may be free from $Ca^{2+}$ and $Mg^{2+}$. For example, the cells may be rinsed with calcium and magnesium free PBS. In the trypsinization step, an amount of dispersing agent in buffer is added to the vessel, and the vessel rolled to coat the growing surface with the dispersing agent solution. For example, 1 ml of trypsin in Hank's BSS may be added to a flask.

In the incubation step, the cells are left for some time at a maintained temperature. For example, the cells may be left at 37° C. for a few minutes (e.g., 2 to 5 minutes). In the dislodging step, the cells may be dislodged by mechanical action, for example by scraping or by whacking the side of the vessel with a hand. The cells should come off in sheets and slide down the surface.

In the quenching step, a volume of medium is added to the flask. The medium may comprise a neutralising agent to stop the action of the dispersing agent. For example, if the dispersing agent is a protease such as trypsin, the medium may contain a protein, such as a serum protein, which will mop up the activity of the protease. In a particular example, 3 ml of serum containing cell culture medium is added to the flask to make up a total of 4 mls. The cells may be pipetted to dislodge or disperse the cells.

In the re-seeding step, the cells are re-seeded into fresh culture vessels and fresh medium added. A number of re-seedings may be made at different split ratios. For example, the cells may be reseeded at 1/15 dilution and 1/5 dilution. In a particular example, the cells may be re-seeded by adding 1 drop of cells into a 25 $cm^2$ flask and 3 drops into another to re-seed the culture, and 7-8 mls media is then added to each to provide for 1/15 dilution and 1/5 dilution from for example a 75 $cm^2$ flask. In the aliquoting step, the cells may be aliquoted into new dishes or whatever split ratio is desired, and media added.

In a specific embodiment, the method includes the following steps: human ES cells are first grown suspended in non-adherent manner to form embryoid bodies (EBs). 5-10 day old EBs are then trypsinized before plating as adherent cells on gelatine coated tissue culture plates.

Maintenance as Cell Culture

The disaggregated cells may be plated and maintained as a cell culture.

The cells may be plated onto a culture vessel or substrate such as a gelatinized plate. Crucially, the cells are grown and propagated without the presence of co-culture, e.g., in the absence of feeder cells.

The cells in the cell culture may be grown in a serum-free medium which is supplemented by one or more growth factors such as fibroblast growth factor 2 (FGF2) and optionally platelet-derived growth factor AB (PDGF AB), at for example 5 ng/ml. The cells in the cell culture may be split or subcultured 1:4 when confluent, by treatment with trypsin, washing and replating.

Absence of Co-Culture

The cells may be cultured in the absence of co-culture. The term "co-culture" refers to a mixture of two or more different kinds of cells that are grown together, for example, stromal feeder cells.

Thus, in typical ES cell culture, the inner surface of the culture dish is usually coated with a feeder layer of mouse embryonic skin cells that have been treated so they will not divide. The feeder layer provides an adherent surface to enable the ES cells to attach and grow. In addition, the feeder cells release nutrients into the culture medium which are required for ES cell growth. In the methods and compositions described here, the ES and MSC cells may be cultured in the absence of such co-culture.

The cells may be cultured as a monolayer or in the absence of feeder cells. The embryonic stem cells may be cultured in the absence of feeder cells to establish mesenchymal stem cells (MSC).

The dissociated or disaggregated embryonic stem cells may be plated directly onto a culture substrate. The culture substrate may comprise a tissue culture vessel, such as a Petri dish. The vessel may be pre-treated. The cells may be plated onto, and grow on, a gelatinised tissue culture plate.

An example protocol for the gelatin coating of dishes follows. A solution of 0.1% gelatin in distilled water is made and autoclaved. This may be stored at room temp. The bottom of a tissue culture dish is covered with the gelatin solution and incubated for 5-15 min. Remove gelatin and plates are ready to use. Medium should be added before adding cells to prevent hypotonic lysis.

Serum Free Media

The dissociated or disaggregated embryonic stem cells may be cultured in a medium which may comprise a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability allows for improved reproducibility and more consistent performance, and decreases possibility of contamination by adventitious agents.

The serum-free media may comprise KNOCKOUT DMEM™ media (Invitrogen-Gibco, Grand Island, N.Y.).

The serum-free media may be supplemented with one or more components, such as serum replacement media, at a concentration of for example, 5%, 10%, 15%, etc. The serum-free media may comprise or be supplemented with 10% serum replacement media from Invitrogen-Gibco (Grand Island, N.Y.).

Growth Factor

The serum-free medium in which the dissociated or disaggregated embryonic stem cells are cultured may comprise one or more growth factors. A number of growth factors are known in the art, including PDGF, EGF, TGF-a, FGF, NGF, Erythropoietin, TGF-b, IGF-I and IGF-II.

The growth factor may comprise fibroblast growth factor 2 (FGF2). The medium may also contain other growth factors such as platelet-derived growth factor AB (PDGF AB). Both of these growth factors are known in the art. The method may comprise culturing cells in a medium comprising both FGF2 and PDGF AB.

Alternatively, or in addition, the medium may comprise or further comprise epidermal growth factor (EGF). Use of EGF may enhance growth of MSCs. EGF may be used at any suitable concentration, for example 5-10 ng/ml EGF. EGF may be used in place of PDGF. EGF is a protein well known in the art, and is referred to as symbol EGF, Alt.

Symbols URG, Entrez 1950, HUGO 3229, OMIM 131530, RefSeq NM_001963, UniProt P01133.

Thus, we disclose the use of media comprising (i) FGF2, (ii) FGF2 and PDGF and (iii) FGF2 and EGF and other combinations.

FGF2 is a wide-spectrum mitogenic, angiogenic, and neurotrophic factor that is expressed at low levels in many tissues and cell types and reaches high concentrations in brain and pituitary. FGF2 has been implicated in a multitude of physiologic and pathologic processes, including limb development, angiogenesis, wound healing, and tumor growth. FGF2 may be obtained commercially, for example from Invitrogen-Gibco (Grand Island, N.Y.).

Platelet Derived Growth Factor (PDGF) is a potent mitogen for a wide range of cell types including fibroblasts, smooth muscle and connective tissue. PDGF, which is composed of a dimer of two chains termed the A chain and B chain, can be present as AA or BB homodimers or as an AB heterodimer. Human PDGF-AB is a 25.5 kDa homodimer protein consisting of 13.3 kDa A chain and 12.2 B chain. PDGF AB may be obtained commercially, for example from Peprotech (Rocky Hill, N.J.).

The growth factor(s), such as FGF2 and optionally PDGF AB, may be present in the medium at concentrations of about 100 pg/ml, such as about 500 pg/ml, such as about 1 ng/ml, such as about 2 ng/ml, such as about 3 ng/ml, such as about 4 ng/ml, such as about 5 ng/ml. In some embodiments, the medium contains FGF2 at about 5 ng/ml. The medium may also contain PDGF AB, such as at about 5 ng/ml.

Splitting Cells

Cells in culture will generally continue growing until confluence, when contact inhibition causes cessation of cell division and growth. Such cells may then be dissociated from the substrate or flask, and "split", subcultured or passaged, by dilution into tissue culture medium and replating.

The methods and compositions described here may therefore comprise passaging, or splitting during culture. The cells in the cell culture may be split at a ratio of 1:2 or more, such as 1:3, such as 1:4, 1:5 or more. The term "passage" designates the process consisting in taking an aliquot of a confluent culture of a cell line, in inoculating into fresh medium, and in culturing the line until confluence or saturation is obtained.

Selection, Screening or Sorting Step

The method may further comprise a selection or sorting step, to further isolate or select for mesenchymal stem cells.

The selection or sorting step may comprise selecting mesenchymal stem cells (MSC) from the cell culture by means of one or more surface antigen markers. The use of a selection or sorting step further enhances the stringency of sorting and selection specificity for MSCs and furthermore potentially reduces possible contamination from embryonic stem cells such as hESCs and other hESC-derivatives from the starting material. This would then further reduce the risk of teratoma formation and further increase the clinical relevance of the protocol we describe.

A number of methods are known for selection or sorting based on antigen expression, and any of these may be used in the selection or sorting step described here. The selection or sorting may be achieved by means of fluorescence activated cell sorting (FACS). Thus, as known in the art, FACS involves exposing cells to a reporter, such as a labelled antibody, which binds to and labels antigens expressed by the cell. Methods of production of antibodies and labelling thereof to form reporters are known in the art, and described for example in Harlow and Lane. The cells are then passed through a FACS machine, which sorts the cells from each other based on the labelling. Alternatively or in addition, magnetic cell sorting (MACS) may be employed to sort the cells.

We have realised that while a number of candidate surface antigens known to be associated with MSCs e.g. CD105, CD73, ANPEP, ITGA4 (CD49d), PDGFRA, some of the MSC associated surface antigens e.g. CD29 and CD49e are also highly expressed in ES cells such as hESCs and their expression are verified by FACS analysis. The association of a surface antigen with MSCs may not be sufficient to qualify the antigen as a selectable marker for isolating MSCs from ES cells such as hESC. Accordingly, the selection or sorting step may employ antigens which are differentially expressed between MSCs and ES cells.

The selection or sorting step of our method may positively select for mesenchymal stem cells based on the expression of antigens. Such antigens may be identified by, for example, comparing the gene expression profiles of hESCs and hES-CMSCs. In particular embodiments, the selection or sorting may specifically make use of any of the antigens shown in Table E1A and E1B below.

The selection or sorting step of our method may positively select for mesenchymal stem cells based on the expression of antigens which are identified as expressed on MSCs, but not expressed on ES cells such as hESCs.

CD73 is highly expressed on MSCs, while being not highly expressed on hESCs. Both CD73 and CD105 are highly expressed surface antigens in MSCs and are among the top 20 highly expressed surface antigens in hESC-MSCs relative to hESC, the use of either CD73 or CD105 (or both) as selectable marker for putative MSCs will be equally effective in sorting for putative MSCs generated by differentiating hESCs.

Alternatively, or in addition, the selection or sorting step may negatively select against antigens based on surface antigens that are highly expressed as surface antigen on embryonic stem cells (ES cells) such as hESCs, and not mesenchymal stem cells e.g., hESC-MSC. Selection or sorting may be based on known or previously identified hESC-specific surface antigens such as MIBP, ITGB1BP3 and PODXL, and CD24.

FACS analysis confirms the expression of CD24 on hESC but not hESC-MSCs. Therefore, CD24 may be used as a negative selection or sorting marker either on its own, or in conjunction with CD105 as a positive selectable marker for isolating putative MSCs from differentiating hESC cultures.

Exosome Compositions

The exosome composition may include a carrier. As used herein "carrier" describes a material that does not cause significant irritation to an organism and does not abrogate the biological activity and properties of the exosomes described here. Carriers must be of sufficiently high purity and of sufficiently low toxicity to render them suitable for administration to the mammal being treated. The carrier can be inert, or it can possess pharmaceutical benefits, cosmetic benefits or both.

Some non-limiting representative examples of carriers include moisturizing agents or humectants, pH adjusting agents, hair conditioning agents, chelating agents, preservatives, emulsifiers, thickeners, solubilizing agents, penetration enhancers, anti-irritants, colorants and surfactants.

As used herein a "moisturizing agent" is a substance that adds or restores moisture to the skin. Representative examples of moisturizing or humectant agents t include, without limitation, guanidine, glycolic acid and glycolate salts (e.g. ammonium salt and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

As is widely recognized in the art, since the pH of the skin is 5.5, compositions for topical skin application (to avoid irritation) can have a pH value of between about pH 4.0 and about pH 7.0, or between about pH 5.0 and about pH 6.0, or about pH 5.5 or substantially pH 5.5. Hence, a pH adjusting composition is typically added to bring the pH of the composition to the desired value. The compositions therefore may be formulated to have a pH value of about 7.2. Suitable pH adjusting agents include, for example, but are not limited to, one or more adipic acids, glycines, citric acids, calcium hydroxides, magnesium aluminometasilicates, buffers or any combinations thereof.

Suitable hair conditioning agents that may be used include, for example, one or more collagens, cationic surfactants, modified silicones, proteins, keratins, dimethicone polyols, quaternary ammonium compounds, halogenated quaternary ammonium compounds, alkoxylated carboxylic acids, alkoxylated alcohols, alkoxylated amides, sorbitan derivatives, esters, polymeric ethers, glyceryl esters, or any combinations thereof.

Hair stimulating agents may be added to the compositions described here. For example, PROCAPIL® (FR 2 791 684 and WO0058347) promotes the visible appearance of thicker and fuller hair and prevents premature hair thinning and hair loss by boosting the synthesis of components at the epidermal junction where the hair anchors to the skin, which helps to anchor the hair follicles more firmly to the scalp. U.S. Pat. No. 6,861,077 describes methods to protect keratinous fibers from extrinsic damages comprising application of compositions comprising at least one plant extract. For example, a plant extract composed of purified glycoproteins obtained from white potatoes (Solanum tuberosum L. is commercially available from SEDERMA, Inc. (France) as DERMOLECTINE® and CAPILECTINE®. ANCRIN® (Sederma), a hydroglycolic solution containing octylbutyrate and glutamine peptide, reduces hair loss by supplying a vegetable substrate to transglutaminases, a group of enzymes known to increase protein reticulation in the scalp and help anchor the hair to the scalp. CAPISOME® (Sederma) is a liposome that comprises homotaurine (3-aminopropane sulfonic acid), a bacterial filtrate of biotechnological origin from enterobacteria that contains high levels of peptides and the sulfur-containing amino acids methionine and cysteine; and marine sulfopolysaccharides. (See U.S. Pat. No. 6,376,557, incorporated herein by reference). CAPIGEN® (Sederma), is a complex that comprises homotaurine (3-aminopropane sulfonic acid), a bacterial filtrate obtained from a strain of microorganisms cultured in a medium comprising selected peptides, with the filtrate containing high levels of peptides, and a sulfomuycopolysaccharide of marine origin, which is a complex of sulfated polysaccharides that are soluble in water and are found in the connective tissue and synovial fluids. FOLLICUSAN™ (Chemlishes Laboratorium Dr. Kurt Richter GmbH), is composed of a fraction derived from milk, ethyl pantenol, inositol and sulfur-containing amino acids (N-acetylcysteine and N-acetyl methionine in an aqueous alcoholic medium. Anageline ANAGELINE™ (Silab) contains an extract from white sweet lupine. CAPILLISIL® (Exsymol S.A.M. of Monaco) is a 20% solution of dimethylsilanediol salicilate in butylenes glycol with triethanolamine. Mahanimba is an extract of the flowers and inflorescence of the neem tree (Melia azadirachta) and contains carotinoids, amino acids, phytosterols, mucins, polyacetylenes, and sea quiterpenes. Malkagni is an extract of the seeds, leaves and flowers of the intellect tree (Celastrus paniculata) and contains tannins, mineral salts, saponins, and iridic glycosides. FITOPUR B™ is a complex available from Sederma, Inc., and comprises extracts of three plants: buchu (Buc hu barosma), henna (Lawsonia inermis), and venus hair (Adiatium capillus-veneris). The essential oil of buchu contains the terpenic oil diosphenol and sulfur compounds. The leaves of henna contain flavonic pigments, including luteoline and laxanthones, principally lawsone. Venus hair is a small fir native to the south of France; it has diuretic and emollient activity. Peptide-copper complexes containing dipeptides or tripeptides chelated to copper stimulate hair growth (see U.S. Pat. Nos. 5,538,945 and 6,017,888, incorporated herein by reference). Hormone replacement therapy (HRT), including administration of micronized progesterone pills and creams and estrogen pills and creams, is used to treat androgenetic alopecia for women. Other such agents are known by persons of skill in the art.

Chelating agents are optionally added to the exosome compositions so as to enhance the preservative or preservative system. Chelating agents that are mild agents, such as, for example, ethylenediaminetetraacetic acid (EDTA), EDTA derivatives, or any combination thereof, are particularly useful.

Suitable preservatives for use in the compositions of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

"Emulsifiers" as used herein promote the formation and stabilization of an emulsion. Suitable emulsifiers may be natural materials, finely divided solids, or synthetic materials. Natural emulsifying agents may be derived from either animal or vegetable sources. Those from animal sources include gelatin, egg yolk, casein, wool fat, or cholesterol. Those from vegetable sources include acacia, tragacanth, chondrus, or pectin. Vegetable sources specifically from cellulose derivatives include methyl cellulose and carboxymethyl cellulose to increase the viscosity. Finely divided emulsifiers include bentonite, magnesium hydroxide, aluminum hydroxide, or magnesium trisilicate. Synthetic agents include anionic, cationic or nonionic agents. Particularly useful are sodium lauryl sulfate, benzalkonium chloride or polyethylene glycol 400 monostearate, or any combinations thereof.

"Thickeners" as used herein refer to agents that make the exosome composition dense or viscous in consistency. Suitable thickeners that may be used include, for example, nonionic water-soluble polymers such as hydroxyethylcellulose (commercially available under the Trademark Natrosol 250 or 350), cationic water-soluble polymers such as Polyquat 37 (commercially available under the Trademark Synthalen CN), fatty alcohols, fatty acids, anionic polymers, and their alkali salts and mixtures thereof.

As used herein, the term "solubilizing agents" refers to those substances that enable solutes to dissolve. Representative examples of solubilizing agents that are usable include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEEN and spans, e.g., TWEEN 80. Other solubilizers that are usable for the compositions described here are, for example, polyoxyethylene sorbitan fatty acid ester, polyoxyethylene n-alkyl ethers, n-alkyl amine n-oxides, polyoxamers, organic solvents, such as acetone, phospholipids and cyclodextrins.

The term "penetration enhancer" as used herein refers to an agent known to accelerate the delivery of a substance through the skin. Suitable penetration enhancers include, but are not limited to, a vegetable oil. Such oils include, for example, safflower oil, cottonseed oil and corn oil.

Additional thickeners, penetration enhancers and other adjuvants may generally be found in Remington's Pharmaceutical Sciences, 18th or 19th editions, published by the Mack Publishing Company of Easton, Pa. which is incorporated herein by reference.

As used herein, an "anti-irritant" refers to an agent that prevents or reduces soreness, roughness, or inflammation of a bodily part. Suitable anti-irritants include, for example, steroidal and non steroidal anti-inflammatory agents or other materials such as aloe vera, chamomile, alpha-bisabolol, cola *nitida* extract, green tea extract, tea tree oil, licorice extract, allantoin, caffeine or other xanthines, glycyrrhizic acid and its derivatives.

The presently known anti-irritants can be divided into water-soluble anti-irritants and water-insoluble anti-irritants. Representative examples of such compositions are described, for example, in U.S. Pat. No. 5,482,710 which is herein incorporated by reference.

Colorants may also be used in the compositions. Colorants include pigments or dyes or a combination thereof as the cosmetic benefit requires. Examples of pigments include, but are not limited to, iron oxides, and titanium oxides. Suitable dyes include FD&C approved colorants, D&C approved colorants, and those approved for use in Europe and Japan (see Marmion, D. M., Handbook of US Colorants for Food, Drugs, Cosmetics, and Medical Devices, 3rd ed, 1991 herein incorporated by reference). The term "color" as used herein refers to the quality of an object or substance with respect to light reflected or absorbed by the object or substance. The three characteristics of color are hue, intensity, and value. "Hue" refers to a gradation, tint, or variety of a color. "Intensity", "chroma", and "saturation" are used interchangeably to refer to the strength or sharpness of a color. A color is full in intensity only when pure and unmixed. "Value" refers to a degree of lightness or darkness in a color.

The term "surfactants" as used herein refers to surface-active substances, such as a detergent. Suitable surfactants include, but are not limited to, sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isothionates, glycerylether sulfonates, sulfosuccinates and combinations thereof. The anionic surfactant may be selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

A pharmaceutically acceptable carrier may also be included in the composition. As used herein the term "pharmaceutically acceptable carrier" refers to any substantially non-toxic carrier conventionally useable for topical administration of pharmaceuticals in which the exosome will remain stable and bioavailable when applied directly to skin or mucosal surfaces.

The compositions described here may include a cosmetically acceptable carrier. As used herein the phrase "cosmetically acceptable carrier" refers to a substantially non-toxic carrier, conventionally useable for the topical administration of cosmetics, with which exosomes will remain stable and bioavailable. It will be understood that cosmetically acceptable carriers and pharmaceutically acceptable carriers are similar, if not often identical, in nature.

Suitable pharmaceutically acceptable carriers include water, petroleum jelly (Vaseline), petroleum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, alcohols, polyols, and the like. Also included are the carriers described hereinabove.

The pharmaceutically acceptable carrier may include a sustained release or delayed release carrier. The carrier can be any material capable of sustained or delayed release of the exosome to provide a more efficient administration resulting in less frequent and/or decreased dosage of the exosome, ease of handling, and extended or delayed effects on epithelial-related conditions. Non-limiting examples of such carriers include liposomes, microsponges, microspheres, or microcapsules of natural and synthetic polymers and the like. Liposomes which may enhance the localized delivery of the exosomes within skin layers, may be formed from a variety of phospholipids, such as cholesterol, stearylamines or phosphatidylcholines.

Suitable cosmetically acceptable carriers are described in the CTFA International Cosmetic Ingredient Dictionary and Handbook, 8th edition, edited by Wenninger and Canterbery, (The Cosmetic, Toiletry, and Fragrance Association, Inc., Washington, D.C., 2000), which is herein incorporated by reference. Also included are the carriers described hereinabove.

The compositions may further include one or more additional compatible active ingredients, which are aimed at providing the composition with another pharmaceutical, cosmeceutical or cosmetic effect, in addition to that provided by a exosome. "Compatible" as used herein means that the components of such a composition are capable of being combined with each other in a manner such that there is no interaction that would substantially reduce the efficacy of the composition under ordinary use conditions.

Wound Healing

We describe the use of an exosome a method for promoting healing of a wound (including optionally of promoting hair growth) in an animal such as a mammal in need thereof. The method for promoting healing of a wound may comprise administering to the animal such as a mammal in need thereof, an effective amount of an exosome.

The term "promoting healing of a wound" as used in this document refers to augmenting, improving, increasing, or inducing closure, healing, or repair of a wound. Wound healing is considered to be promoted, for example, if the time of healing a wound treated with exosome compared to a wound not treated with exosome is decreased by about 10%, such as decreased by about 25%, such as decreased by about 50%, such as decreased by about 75%.

Alternatively, wound healing is considered to be promoted if the time and extent of re-acquisition of muscle contractility and function treated with exosome compared to a wound not treated with exosome is improved by about by about 10%, such as improved by about 25%, such as improved by about 50%, and such as improved by about 75%. Conversely, the degree of scar formation can be used to ascertain whether wound healing is promoted.

Thus, the terms "treating" and "treatment" should broadly be considered as referring to administering to a subject a therapeutically effective amount of an exosome composition so that the subject has an improvement in the disease. The improvement may comprise any improvement or remediation of the symptoms. The improvement may comprise an observable or measurable improvement. Thus, a treatment may improve the disease condition, but may not be a complete cure for the disease.

The wound healing may be promoted in the animal by a number of ways. One example is that the wound healing may be promoted by promoting regeneration of skeletal muscle. Muscle tissue generally regenerate from reserve myoblasts called satellite cells. The satellite cells are typically found distributed throughout muscle tissue. In undamaged muscle, the majority of satellite cells are quiescent in that they neither differentiate nor undergo cell division.

Following muscle injury or during recovery from disease, satellite cells re-enter the cell cycle, proliferate, and enter existing muscle fibres or undergo differentiation into multinucleate myotubes which form new muscle fibre. The myoblasts eventually yield replacement muscle fibres or fuse into existing muscle fibres, thereby increasing fibre girth.

Thus, the term "regeneration of skeletal muscle" may be used to refer to the process by which new skeletal muscle fibres form from muscle progenitor cells. The new skeletal muscle fibres can be new skeletal muscle fibres that replace injured or damaged muscle fibres or new skeletal fibres that fuse into existing muscle fibres.

Skeletal muscle regeneration may be considered to be promoted if the number of new fibres is increased at least about 1%, such as at least by about 20%, such as by at least about 50%.

The wound healing may alternatively or in addition be promoted in the animal such as a mammal by promoting collagen production. Collagen is a fibrous structural protein and a major component of the extracellular matrix. Any type of collagen may be promoted. Examples of types of collagen include, but are not limited to, collagen types I-XXVIII. For example, the collagen may comprise type I, collagen type III, collagen type IV, or collagen type VI.

The term "promoting collagen production" may be used to refer to an increase in the amount of collagen produced. Any method known to those skilled in the art can use used to determine whether the production of collagen is increased. For example, an increase in collagen production can be determined by analyzing for increased expression of collagen by using, for example, Northern Blot, real time RTPCR, etc. Typically, collagen production is considered to be promoted if the amount of collagen is increased by at least about 1%, such as at least by about 10%, such as by at least about 20%.

Wounds

The wound can be an internal wound or an external wound found in any location of an animal such as a mammal.

A wound is typically caused by physical means, such as mechanical, chemical, bacterial, or thermal means. Wounds can also be caused by accidents, such as a car accident, a fall, injuries sustained in battle (deep lacerations and amputations in soldiers), etc. or by surgical procedures, such as open heart surgery, organ transplants, amputations, and implantations of prosthetics, such as joint and hip replacement, etc. The wound can be an open wound or closed wound.

Open wounds refers to wounds in which the skin is broken. Open wounds include, for example, incisions (i.e., wounds in which the skin is broken by, for instance, a cutting instrument (e.g., knife, razor, etc.)), lacerations (i.e., wounds in which the skin is typically broken by a dull or blunt instrument), abrasions (e.g., generally a superficial wound in which the topmost layers of the skin are scraped off), puncture wounds (typically caused by an object puncturing the skin, such as nail or needle), penetration wounds (e.g., caused by an object such as a knife), and gunshot wounds.

Closed wounds are typically wounds in which the skin is not broken. An example of a closed wound is a contusion.

The wound may comprise an acute wound. An "acute wound" as used in this document may refer to a wound that heals in a relatively short amount of time. Acute wounds have a relatively rapid rate of healing, especially in healthy subjects. However, in the elderly or immunocompromised healing can be prolonged. Healing is also prolonged if the wound becomes infected. Examples of acute wounds include, but are not limited to partial-thickness burn, laceration, bullet wound or infected wound.

The wound may comprise an chronic wound. A "chronic wound" as used in this document may refer to wounds that take a long time to heal or that do not heal without external intervention. Still further, a chronic wound can also include infected wounds that take a long time to heal.

Examples of chronic wounds or chronic ulcers include, but are not limited to diabetic ulcers, venous stasis ulcers, decubitus or pressure ulcers. Yet further, chronic wounds can also include infected wounds. Chronic wounds are wounds that do not repair or do so extremely slowly, and show partial or total lack of structural organization and functional coordination with normal tissue. Chronic wounds or chronic ulcers can be broadly classified into three major types: diabetic ulcers, venous stasis ulcers, decubitus or pressure ulcers. Diabetic ulcers often occur on a foot. Chronic diabetic state and poor glucose control results in poor peripheral circulation and microcirculation due to progressive arteriosclerosis; neuropathic changes that result in an insensate extremity prone to trauma; and intrinsic defects in the wound healing process that may include reduced abundance and response to cellular growth factors. In the case of venous ulcers, venous hypertension causes disturbed microcirculation and pathological changes of the capillaries, elevated persistent levels of pro-inflammatory cytokines and proteases. Fibroblast senesce and respond less to growth factors, which distribute unfavorably. Proteolytic enzymes and their inhibitors are imbalanced. Pressure ulcers occur when skin is under pressure without movement to allow blood flow for 8-12 hours.

The wound may comprise a skin wound. Skin wounds further comprise but are not limited to full-thickness wounds and partial-thickness wounds. Full-thickness wounds involve the complete removal of epidermis and dermis to the depth of fascial planes or subcutaneous fat. In the loose-skinned species, the thin musculature of the *panniculus carnosus*, which firmly adheres to the base of the dermis, is usually removed as well. In partial-thickness wounds a substantial amount of dermis, mostly reticular, is left behind, and, more importantly, the bases of most epidermal appendages (sebaceous and sweat glands, hair follicles) remain intact.

The term "wound" as used here may therefore include any injury to any portion of the body of a subject including, but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, incisions, excoriations, those injuries sustained in automobile and other mechanical accidents, and those caused by bullets, knives and other weapons, ulcer such as pressure ulcer, plaster ulcer and decubitus ulcer, and post-surgical injuries, as well as chronic conditions such as pressure sores, bedsores, conditions related to diabetes and poor circulation, and all types of acne. In addition, said wound includes dermatitis such as impetigo, intertrigo, folliculitis and eczema.

Other examples of wounds include, but are not limited to skin wound, internal wound, gastrointestinal wound, oral wound, bone wounds, ophthalmic wound, surgical wound, or any combination thereof. Wounds can be found on but not limited to skin, internal organs, stomach and intestines (gastrointestinal), oral mucosa, and eye (ophthalmic wounds, e.g., corneal ulcers, radiokeratomy, corneal transplants, epikeratophakia and other surgically induced wounds in the eye). Depending on the process that causes the wounds, wounds can also be classified as but are not limited to incisional wounds, excisional wounds, diabetic ulcers, venous stasis ulcers, decubitus or pressure ulcers, chemical wounds, and burn wounds.

Areas of the body which can be treated may include, but are not limited to, skin, muscle and internal organs.

Any animal such as a mammal suffering from a wound, such as those described above, may be considered in need of promoting wound healing as described in this document. The term "subject" may therefore be used to refer to a human or lower animal on whom the methods and compositions described here are practiced.

For example, the exosome composition may be employed to treat a human subject.

Therapeutic Methods

An exosome may be orally, topically, or parenterally administered to a subject suspected of or having a wound.

One of skill in the art can determine the therapeutically effective amount of the composition to be administered to a subject based upon several considerations, such as absorption, metabolism, method of delivery, age, weight, disease severity and response to the therapy. Oral administration of the composition includes oral, buccal, enteral or intragastric administration. It is also envisioned that the composition may be used as a food additive. For example, the composition is sprinkled on food or added to a liquid prior to ingestion. Topical administration of the composition includes topical, dermal, epidermal, or subcutaneous administration. Parenteral administration includes, but is not limited to intramuscular, intravenous, intraperitoneal, intraoccular or intraarticular administration or administration into a surgical field.

The exosome may be administered in an effective amount to seal, to close, to improve or to repair the wound. Also, it is envisioned that the composition described here may also decrease, reduce, or inhibit, bacterial infections of the wound, which aid in the healing process of a wound.

Treatment regimens may vary as well, and often depend on wound type, wound location, wound and/or healing progression, and health and age of the patient. Obviously, certain types of wounds will require more aggressive treatment, while at the same time, certain patients cannot tolerate more taxing protocols. The clinician will be best suited to make such decisions based on the known efficacy and toxicity (if any) of the therapeutic formulations.

The composition may be given in a single dose or multiple doses. The single dose may be administered daily, or multiple times a day, or multiple times a week, or monthly or multiple times a month. The composition may be given in a series of doses. The series of doses may be administered daily, or multiple times a day, weekly, or multiple times a week, or monthly, or multiple times a month. Thus, one of skill in the art realizes that depending upon the wound type, location, health of the subject, etc., the exosome composition described here may be administered for any given period of time until the wound is healed at least by 5%, 10%, 20%, 30%, 40%, 50%, 55%, 60%, 65%, 70%, 75%, 80%, 85%, 90%, 95% or 100% or any range in between.

For topical administration, a gel formulation comprising exosomes may be used to coat fibres of an absorbent gauze dressing to form a wound healing bandage which may then be placed on a wound. A low viscosity formulation may be used. The wound healing bandage may be prepared by soaking a gauze dressing with an aqueous gel solution comprising exosomes having wound healing activity. The bandage can then be applied to the wound so that the coated fibres of the gauze contacts the wound and stimulate the rate of wound healing.

Where a gel comprising exosomes is applied to an internal or incisional wound, the gel forming polymer may be biodegradable. The naturally occurring polymers are generally biodegradable. Examples of these are collagen, the glycosaminoglycans, gelatin and starch. The cellulosics are not biodegradable. The synthetic polymers such as the vinyl polymers are not degradable. The biodegradability of the polymers described herein is well known to those skilled in the art.

We further describe a method of treating a wound comprising the step of supplementing the local immune system by increasing the amount of exosome in the vicinity of the wound. The exosomes may be administered topically to the wound.

We also describe a method of treating a wound comprising the step of supplementing the systemic immune system by increasing the amount of exosome in the systemic circulation. The exosomes may be administered via a parenteral route, which includes, but is not limited to intramuscular, intravenous, intraperitoneal, intraoccular, intraarticular or into a surgical field.

We further disclose a method of treating a wound comprising the step of supplementing the mucosal immune system by increasing the amount of exosomes in the gastrointestinal tract of the subject.

We describe a method of enhancing the immune system of a subject suffering from a wound by administering to the subject an exosome composition. Depending upon the mode of administration, different arms of the immune system are enhanced. For example, topical administration of the composition results in enhancement of the local immune system, i.e., in the vicinity of the wound. Parenteral administration of the composition results in enhancement of the systemic immune system. Yet further, oral administration of the composition results in enhancement of the mucosal immune system, which can also result in systemic effects as well.

The immune system, whether local, systemic or mucosal, may be enhanced by exosomes stimulating cytokines and/or chemokines. Exemplary cytokines include interleukin-18 and GM-CSF in the gastrointestinal tract, which are known to enhance immune cells or stimulate production of immune cells. For example, interleukin-18 enhances natural killer cells or T lymphocytes, which can kill bacteria infecting a wound. For example, interleukin-18 (IL-18) enhances CD4+, CD8+ and CD3+ cells. It is known by those of skill in the art that IL-18 is a Th.sub.1 cytokine that acts in synergy with interleukin-12 and interleukin-2 in the stimulation of lymphocyte IFN-gamma production. Other cytokines or chemokines may also be enhanced for example, but not limited to IL-12, IL-1b, MIP-3α, MIP-1α, or IFN-gamma. Other cytokines or enzymes may be inhibited for example, but not limited to IL-2, IL-4, IL-5, IL-10, TNF-α, or matrix metalloproteinases. It is further contemplated that IL-18 or GM-CSF stimulate the production or activity of cells involved in wound repair, for example, but not limited to keratinocytes, endothelial cells, dendritic cells, fibroblasts, and myofibroblasts. Yet further, it is envisioned that exosomes inhibit the production of TNF-alpha, which inhibits cells involved in inflammation.

The local immune system in a subject may be boosted by administering topically a therapeutically effective amount of an exosome composition in the vicinity of the wound can result in the killing of bacteria infecting the wound. Topical administration of an exosome composition may stimulate the production of a cytokine or a chemokine. Exemplary cytokines that can be stimulated by exosomes may include, but are not limited to interleukin-18 (IL-18), interleukin-12 (IL-12), granulocyte/macrophage colony-stimulating factor (GM-CSF), and gamma interferon (IFN-γ). Exemplary chemokines include, but are not limited to macrophage inflammatory protein 3 alpha (MIP-3α), macrophage inflammatory protein 1 alpha (MIP-1α), or macrophage inflammatory protein beta (MIP-1β).

The exosome composition may also result in inhibition of a cytokine or chemokine. The cytokines include, but are not limited to interleukin-2 (IL-2), interleukin-4 (IL-4), interleukin-5 (IL-5), interleukin-10 (IL-10), and tumor necrosis factor alpha (TNF-α). Still further, the exosome composition can also inhibit the production of matrix metalloproteinases (MMPs).

Cytokines, for example, interleukin-18 or granulocyte/macrophage colony-stimulating factor, can stimulate the production or activity of immune cells. The immune cells include, but are not limited to T lymphocytes, natural killer cells, macrophages, dendritic cells, and polymorphonuclear cells. More specifically, the polymorphonuclear cells are neutrophils and the T lymphocytes are selected from the group consisting of CD4+, CD8+ and CD3+ T cells.

Cytokines, for example, interleukin-18 or granulocyte/macrophage colony-stimulating factor, can also stimulate the production or activity of cells involved in wound repair. The cells involved in wound repair include, but are not limited to keratinocytes, endothelial cells, fibroblasts, dendritic cells, and myofibroblasts. The inhibition of TNF-alpha further inhibits the migration and maturation of dendritic cells. The dendritic cells can be Langerhans cells.

Administration

We disclose method of treating a skin wound (and/or of promoting hair growth), the method comprising the step of administering a therapeutically effective amount of a exosome to a subject having the skin wound to result in an improvement or a remediation of a symptom of the skin wound.

The exosome may be applied in any suitable quantity. For example, a composition containing 10 μg or less, such as 5 μg or less, such as 2 μg or less, such as 1 μg or less, such as 0.5 μg or less, such as 0.3 μg of exosome may be applied to subject.

The pharmaceutical composition may comprise 40 μg/ml or less, 20 μg/ml or less, 8 μg/ml or less, 4 μg/ml or less, 2 μg/ml or less or 1.2 μg/ml or less of exosome.

The composition may be administered for any suitable length of time, such as at least one week to twelve weeks. The amount of exosome that is administered may comprise any suitable amount, such as about 0.0001 milligram to about 100 g per day.

The exosome may be administered to an animal such as a mammal in need thereof. The animal may be a farm animal, such as a goat, horse, pig, or cow; a pet animal, such as a dog or cat; a laboratory animal, such as a mouse, rat, or guinea pig; or a primate, such as a monkey, orangutan, ape, chimpanzee, or human. For example, the mammal may be a human.

The exosome can be incorporated in a pharmaceutical composition suitable for use as a medicament, for human or animal use. Pharmaceutical compositions are described in further detail below.

An effective amount of the exosome, such as in a pharmaceutical composition, may be administered to a human or an animal in need thereof by any of a number of well-known methods. For example, the exosome may be administered systemically or locally, for example by injection.

The systemic administration of the exosome may be by intravenous, subcutaneous, intraperitoneal, intramuscular, intrathecal or oral administration. Alternatively, the exosome may be applied topically in appropriate situations. Such situations include, for example, skin abrasions and surface wounds.

An effective amount of a pharmaceutical composition described here may comprise any amount that is effective to achieve its purpose. The effective amount, usually expressed in mg/kg can be determined by routine methods during pre-clinical and clinical trials by those of skill in the art.

Combination Therapy

In order to increase the effectiveness of the exosome composition, it may be desirable to combine the exosome composition with other agents effective in the treatment of wounds, such as growth factors, skin replacement therapy, enzymatic and surgical debridement, moist wound dressings, cleansers, antibiotics.

Such wound healing agents are capable of negatively affecting a wound in a subject, for example, by enhancing the growth rate of skin cells, augmenting the blood supply to skin cells, promoting an immune response against bacteria infecting the wound, killing bacteria, cleaning ischemic tissue, promoting the closure of the wound. More generally, these other wound healing agents are provided in a combined amount effective to promote the healing of a wound.

This process may involve administering the exosome composition and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the exosome composition and the other includes the second agent(s).

Alternatively, the exosome composition may precede or follow the other wound healing agent treatment by intervals ranging from minutes to weeks. Where the other wound healing agent and exosome composition are administered or applied separately to the wound, one would generally ensure that a significant period of time did not expire between the time of each delivery, such that the agent and exosome composition would still be able to exert an advantageously combined effect on the wound. In such instances, it is contemplated that one may contact the wound with/administer both modalities within about 1-14 days of each other and, such as, within about 12-24 hours of each other. In some situations, it may be desirable to extend the time period for treatment significantly, however, where several days (2, 3, 4, 5, 6 or 7) to several weeks (2, 3, 4, 5, 6, 7 or 8) lapse between the respective administrations.

Growth Factors Wound healing therapies include growth factor based treatments. Examples include, but are not limited to Regranex™ (Becaplermin-BB gel), AuTolo-Gel (autologous activated platelet releasate), Procuren (autologous thrombin-induced platelet releasate). Growth factors act without limitation by promoting granulation or the formation of new highly vascularized connective tissue; stimulating proliferation, differentiation and migration of epithelial cells, vascular endothelial cells and other skin cells; enhancing the production of collagen, collagenase, and extracellular matrix.

Skin Replacement Therapy

Examples include but are not limited to Apligraf (bilayered living skin), Trancyte (Human fibroblast-derived temporary skin substitute), Dermagraf (permanent, one-layer skin substitute), Epicel (living one-layer artificial skin), Integra (collagen-based skin regeneration template), AlloDerm (single-layer artificial skin made from human cadavers), CCS (living, cultured, artificial skin).

Enzymatic and Surgical Debridement

Debridement is a process or procedure to clean ischemic or dead tissue. Enzymatic debriders include Accuzyme papain-urea debriding ointment and Collagenase Santyl. Surgical debridement refers to physical removal of at least part of the ischemic or dead tissue in a wound. Debridement may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. Enzymatic debridement treatments may be of varying dosages as well. The methods and compositions described here may also be used in conjunction with enzymatic or surgical debridement.

Dressings

Wound healing therapies include a variety of treatments based on dressings. Dressing categories include but are not limited to amorphous hydrogels, hydrogel sheets, absorptives, alginates, biological and synthetic dressings, collagens, composites, contact layers, elastic gauzes, foams, gauzes and non-woven dressings, hydrocolloids, impregnated dressings, silicone gel sheets, silver dressings, transparent films, wound fillers Cleansers Examples include but are not limited to Biolex, Lamin, Wound Wash Saline, Techni-Care, CarraKlenz, DiaB Klenz, MicroKlenz, RadiaCare Klenz, UltraKlenz, Comfee Sea-Clens, Optipore Sponge, Saf-Clens, Shur-Clens, Dermagran, DermaKlenz, Dumex, Gene Klenz, GRX, Allclenz, Restore, Hyperion, Medi Tech, Skintegrity, MPM Antimicrobial, ClinsWound, Septicare, Lobana Saline.

Antimicrobials

Examples of include but are not limited to Sulfamylon Cream, Thermazene Cream (1% silver sulfadiazine), cadexomer-iodine pads or gel. Examples of intravenous antimicrobials include but are not limited to imipenem/cilastatin, β-lactam/β-lactamase inhibitors (ampicillin/sulbactam, piperacillin/tazobactam), and broad-spectrum cephalosporins (cefoxitin, ceftizoxime, ceftazidime). Other examples include, but are not limited to Bensal HP, Barri-Care, Care-Creme, Formula Magic, Baza, Micro-Guard, Ca-Rezz, Diabet-X products, Mitrazol Powder, PiercingCare, Triple Care products, and various antifungal creams and powders.

Compression

Dynamic compression examples, include pumps and sleeves such as but not limited to ArtAssist, ArterialFlow, EdemaFlow, PulStar, Circulator Boot, Flowplus, Flowpress, Flowtron. Static compression include but are not limited to leg wrappings, gloves, socks, leg wears, leg supports, arm sleeves, stasis pads, compression hosieries, non-elastic bands, high compression bandages, zinc impregnated bandages, elastic bandages.

Oxygen Therapy

Examples of systemic hyperbaric oxygen therapy include but are not limited to compartments for one patient to lay down, for one patient to sit up to 25 degree angle, for one patient to sit up to 90 degree angle, for more than one patient to be treated simultaneously. Examples of topical hyperbaric oxygen therapy include but are not limited to disposable topical hyperbaric oxygen systems for extremity ulcers, disposable topical hyperbaric oxygen systems for decubitis, post-op and trauma wounds.

Hydrotherapy, Electric Therapy

Examples include but are not limited to dry hydrotherapy machines; non-contact thermal wound care systems for use on partial- and full-thickness wounds that maintain warmth and humidity in the wound area; systems that provide non-thermal, pulsed high frequency, high peak power, electromagnetic energy to treat edema and pain in acute and chronic wounds; systems that use controlled, localized negative pressure and support for moist wound healing; pulsatile irrigators with controllable pressures below 15 psi for site-specific treatment of various wounds with variety of tips; various wound irrigation and whirlpool systems.

Nutritional Therapy Products

Examples include but are not limited to isotonic, high-protein, fibre-containing tube feedings to support wound healing; high-protein, cholesterol-free nutritional supplements.

Cohesives, Glues, Sealants, Patches

Examples include but are not limited to Dermabond, CoStasis, CoSeal, BioGlue, FibRx, FocalSeal, FloSeal, AutoSeal, Indermil, Syvek, LiquiSheild, LiquiBand, Quixil, CryoSeal, VIGuard Fibrin Sealant, and various tapes, closures, and securement products.

Topical Wound Healing Promoters

Examples include but are not limited to topical aerosols which stimulate the capillary bed of chronic wounds; skin protectants with zinc-nutrient formulations; topical gels to help scars feel softer and smoother; hydrophilic ointments that cleanse degraded proteins, promote healthy granulation, control local inflammation and reduce wound odors; oil-and-water wound dressing emulsions that selectively recruit macrophages.

Other Biotherapy Agents

Adjuvant therapy may also be used in conjunction with the methods and compositions described here. The use of adjuvants or immunomodulatory agents include, but are not limited to tumor necrosis factor; interferon alpha, beta, and gamma; IL-2 and other cytokines; F42K and other cytokine analogs; or MIP-1, MIP-1beta, MCP-1, RANTES, and other chemokines.

Pharmaceutical Compositions

The exosome composition may be contained in a pharmaceutical carrier. It may be provided in the form of a pharmaceutical composition.

A exosome composition suitable for administration is provided may be provided in a pharmaceutically acceptable carrier with or without an inert diluent.

The carrier may be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods described here may be appropriate. Examples of carriers or diluents include fats, oils, water, saline solutions, lipids, liposomes, resins, binders, fillers and the like, or combinations thereof.

The exosome composition may be combined with the carrier in any convenient and practical manner, i.e., by solution, suspension, emulsification, admixture, encapsulation, absorption and the like. Such procedures are routine for those skilled in the art.

For example, the composition may be combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach or in the open wound environment. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. For an orally administered composition, the stabilizer can also include antagonists to the secretion of stomach acids. Yet further, for a topically administered composition, the stabilizer can also include antagonists to skin acids.

The composition for oral administration which is combined with a semi-solid or solid carrier can be further formulated into hard or soft shell gelatin capsules, tablets, or pills. For example, gelatin capsules, tablets, or pills are enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the exosome composition to be released and absorbed by specialized cells, e.g., epithelial enterocytes and Peyer's patch M cells.

Further, the composition for topical administration which is combined with a semi-solid carrier can be further formulated into a gel ointment. An example of a carrier for the formation of a gel ointment is a gel polymer. Gel polymers prevent denaturation of the composition in the open skin by serum proteases. The gel formulation also provides a controlled delivery system for exosome or its activity on a wound site. Controlled delivery refers to drug release or activity release sufficient to maintain a therapeutic level over an extended period of time, such as up to 24 hours or more, such as in the range of 1 to 12 hours. The present gel formulation increases the contact time of the exosome at the wound site and provides a sustained release dosage form necessary to achieve a significant increase in the rate of wound healing. This is an important advantage because it permits less frequent application of the formulation to the wound and thereby permits fewer disturbances to the wound and its cellular components.

The gel formulation described here may adhere to a wound and conform to irregular body or wound contours. The gels may be applied directly to a wound site or in conjunction with a compliant porous or microporous substrate, for example in the form of a coating, to be applied to the wound site. Gels have the further advantages of having a high water content (which keeps the wound moist), the ability to absorb wound exudate, easy application to a wound and easy removal by washing. Gels have a cool feeling when applied to a wound and thus can increase patient comfort and acceptance of the formulation, especially on sensitive wounds.

The aqueous gels described here have different viscosities depending on the intended application of the gel. Viscosity is a measure of the resistance of a liquid to flow. It is defined as the ratio of the shearing stress to the rate of shearing. The shear stress is the resistance of the liquid to flow under the influence of an applied force, i.e., the molecular resistance within a body opposing an external force. The shear stress is defined as the ratio of the force to the area sheared. When a liquid is sheared, assuming laminar flow, the layers of the liquid move at different rates. The relative rate of motion of the layers is only one factor in the rate of shear. The other is the distance, or clearance between the shearing planes. Thus, shear rate is defined as the ratio of the velocity of the gel to the clearance. Viscosity has the dimensions of dynes/sec/cm.sup.2. These dimensions are referred to as poise. The dimensions of viscosity referred to herein, unless otherwise indicated, are in centipoise (cP) as measured using a BROOKFIELD® viscometer. All viscosity values are at room temperature, e.g., 22.degree. C. –25.degree. C., unless otherwise indicated.

The gel forming materials may be water-soluble polymers capable of forming a viscous aqueous solution or non-water soluble, water swellable polymers (e.g., collagen), which can also form a viscous solution. Swellable polymers are those that absorb water rather than dissolve in water. Cross-linked forms of the polymer described herein may not be water soluble but may be water-swellable. Therefore, cross-linked forms of the polymer are envisaged. Cross-linking refers to covalently bonding polymer chains together with a bifunctional reagent such as glutaraldehyde. Also, it is understood by those skilled in the art that certain polymers may have to be used in the salt form or partially neutralized in order to be made water soluble. For example, hyaluronic acid may be used as sodium hyaluronate to provide suitable water solubility.

In the aqueous gel formulations for topical or incisional wound healing, the polymer may be selected from the group consisting of vinyl polymers, polyoxyethylene-polyoxypropylene copolymers, polysaccharides, proteins, poly(ethylene oxide), acrylamide polymers and derivatives or salts thereof. It is understood that poly(ethyleneoxide) includes polyethylene glycol. Where the gel formulations are for use in healing wounds in the anterior chamber of the eye, the polymers may be the same except the polyoxyethylene-polyoxypropylene copolymers or poly(ethylene oxide) should not be used. Also, for anterior chamber use, the polymer may be biodegradable, i.e., it will break down into harmless constituents that can be drained from or metabolized in the anterior chamber. In the low viscosity, aqueous formulations for use in ophthalmic wound healing, the gel forming polymers may be the same as for topical or incisional wound healing, except that poly(ethylene oxide) may not be used.

The vinyl polymers may be selected from the group consisting of polyacrylic acid, polymethacrylic acid, polyvinyl pyrrolidone and polyvinyl alcohol. The polysaccharides may be selected from the group consisting of cellulose or cellulose derivatives, glycosaminoglycans, agar, pectin, alginic acid, dextran, starch, and chitosan. Starch occurs in two forms, α-amylose and amylopectin. The glycosaminoglycans may be selected from the group consisting of hyaluronic acid, chondroitin, chondroitin-4-sulfate, chondroitin-6-sulfate, dermatan sulfate, keratan sulfate, heparin sulfate and heparin. The glycosaminoglycans may be used to enhance wound healing in combination with any other gel-forming polymer. The proteins may be selected from the group consisting of collagen, gelatin and fibronectin. The acrylamide polymers may comprise polyacrylamide or polymethacrylamide polymers. Biocompatible polyacrylamide polymers may be used. Carbomers may comprise polyacrylamide polymer. Carbomers are synthetic high molecular weight polymers of acrylic acid cross linked with either alkyl esters of sucrose or pentaerythritol. Suitable commercially available grades of carbomer include CARBOPOL 910™ (The Lubrizol Corporation, Wickliffe, Ohio), CARBOPOL 934™, CARBOPOL 940™, CARBOPOL 941™, CARBOPOL 971P™, CARBOPOL 974P™, CARBOPOL 980™, CARBOPOL 981™, CARBOPOL 1342™, RHEOGIC 252L™ (Nihon Junyaku), RHEOGIC 250H™, and HOSTACERIN PN73™ (Hoescht U.K. Ltd).

In the gel formulation for topical or incisional wound healing, the viscosity may be within the range 1,000-12,000,000 cps at room temperature. The viscosity range may be 50,000-2,000,000. The topical gel formulation may comprise 0.01-5% by weight polyacrylic acid having an average molecular weight of about 450,000-4,000,000. The polyacrylic acid may be present at 0.5-1.5% by weight and has an average molecular weight of 2,000,000-4,000,000. The pH of the polyacrylic acid gel should be within the range 4.5-8 such as in the range 6.5-7.5.

The incisional gel may comprise 15-60% by weight of a polyoxyethylene-polyoxypropylene block copolymer having an average molecular weight of about 500-50,000. The block copolymer may be present at 15-40% by weight and have an average molecular weight in the range 1,000-15,000. The block copolymers are commonly known as PLURONICS® (BASF Corporation, Ludwigshafen, Germany). Examples of PLURONICS® are PLURONIC® F88 and F127.

The topical or incisional gel may comprise 1 to 20% by weight of a cellulose polymer having a molecular weight of about 50,000 to 700,000. The cellulose polymer may be present at 2-8% by weight and has an average molecular weight in the range 80,000-240,000. Cellulose polymers include hydroxypropylmethyl cellulose (HPMC), carboxymethyl cellulose (CMC) and methyl cellulose (MC).

The topical and incisional gel may comprise 0.5-10% by weight of hyaluronic acid having an average molecular weight in the range 500,000 to 8,000,000. The hyaluronic acid may be present at 1.5-6.0% by weight and the average molecular weight is greater than 1,000,000.

Acrylamide polymers may be useful for all types of wound healing, particularly in the anterior chamber of the eye. An absorbable acrylamide polymer, such as polyacrylamide, may be a good substitute for present carrier systems used in ophthalmic applications, such as hyaluronic acid. The acrylamide polymers may have an average molecular weight in the range 1-13 million, such as about 4-6 million. The weight percent of the acrylamide polymer in the gel may be 2-5%, such as 3.5-4.5%. Substituted acrylamide polymers, such as methyl and alkyl substituted polymers may also be used.

For use in the anterior chamber of the eye, an acrylamide gel delivery system has the following characteristics: any products of the dissolution or degradation of the delivery matrix are nontoxic and do not clog the trabecular mesh work; the gel is optically transparent; and the gel can be left in the anterior chamber without causing adverse clinical effects such as an unacceptable increase in ocular pressure.

It will be readily apparent to one skilled in the art that the desired viscosity range may be achieved by varying the molecular weight and percent concentration of the polymer in the formulation. For example, a gel having a low viscosity may be achieved by using a low molecular weight polymer or a lower percent concentration or a combination of the two. A high viscosity gel may be achieved by using a higher molecular weight polymer and a higher percent concentration. Intermediate viscosities may be achieved by varying the molecular weight and percent concentration accordingly.

The low viscosity solution may comprise 0.01-2.0% by weight polyacrylic acid having an molecular weight of about 100,000-4,000,000. The polymer may be present at 0.05-0.5%. The dilute viscous solution may comprise 2-40% by weight of a polyoxyethylene-polyoxypropylene copolymer having an average molecular weight of 500-500,000. The concentration may be 2-20% and the molecular weight is 1,000-15,000. Alternatively, the dilute viscous solution may comprise a cellulose polymer at 1-20% and having a molecular weight of about 80,000-240,000. The concentration may be in the range of 1-10%. The dilute viscous solution may comprise 0.5-5.0% by weight hyaluronic acid having an average molecular weight of about 500,000-8,000,000. The concentration may be 0.5-2.0% and the average molecular weight is 1,000,000-6,000,000. If the dilute viscous solution is to be used as eye drops, the viscosity may be in the range 1-100 cps. If it is used for other applications, such as soaking a bandage, then any viscosity in the range 1.0-5,000 will be suitable.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules, gel ointments and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

Further Aspects

Further aspects and embodiments of the invention are now set out in the following numbered paragraphs; it is to be understood that the invention encompasses these aspects:

Paragraph 1. Use of an exosome for the preparation of a pharmaceutical composition to promote or enhance wound healing and hair growth in an individual.

Paragraph 2. Use according to Paragraph 1, in which the exosome is derived from a stem cell.

Paragraph 3. Use according to Paragraph 2, in which the stem cell comprises a mesenchymal stem cell (MSC).

Paragraph 4. Use according to Paragraph 1, 2 or 3, in which the exosome has a size of between 50 nm and 100 nm as determined by electron microscopy.

Paragraph 5. Use according to any preceding claim, in which the exosome comprises: (a) a complex of molecular weight>100 kDa, for example comprising proteins of <100 kDa; (b) a complex of molecular weight>300 kDa, for example comprising proteins of <300 kDa; or (c) a complex of molecular weight>1000 kDa.

Paragraph 6. Use according to any preceding claim, in which the exosome has a size of between 2 nm and 200 nm, such as a size of between 50 nm and 150 nm or a size of between 50 nm and 100 nm, for example as determined by filtration against a 0.204 filter and concentration against a membrane with a molecular weight cut-off of 10 kDa, or a hydrodynamic radius of below 100 nm, such as between about 30 nm and about 70 nm, between about 40 nm and about 60 nm, such as between about 45 nm and about 55 nm, such as about 50 nm, for example as determined by laser diffraction or dynamic light scattering.

Paragraph 7. Use according to any preceding claim, in which the time taken for a wound to completely heal (complete wound closure) in a test animal to which the pharmaceutical composition is applied is 90% or shorter, 85% or shorter, 80% or shorter, 75% or shorter, 70% or shorter, 65% or shorter or 50% or shorter than the time taken for complete wound closure in a control animal on which the pharmaceutical composition is not applied.

Paragraph 8. Use according to any preceding claim, in which the mean time taken for complete wound healing in a group of test animals to which the pharmaceutical composition is applied is 90% or shorter, 85% or shorter, 80% or shorter, 75% or shorter, 70% or shorter, 65% or shorter or 50% or shorter than the mean time taken for complete wound closure in a control group of animals on which the pharmaceutical composition is not applied.

Paragraph 9. Use according to Paragraph 7 or 8, in which the mean time for complete wound healing in a group of test animals is 14.6 days or 13 days, or in which the mean time for complete wound healing in a group of control animals is 17 days, or both.

Paragraph 10. Use according to Paragraph 7, 8 or 9, in which the test animal or group of test animals comprise(s) a C57BL/6J female mouse and the wound comprises a biopsy punch of 177 mm$^2$ (15-mm diameter wound).

Paragraph 11. Use according to any of claims 7 to 10, in which an amount of pharmaceutical composition containing 10 μg or less, such as 5 μg or less, such as 2 μg or less, such as 1 μg or less, such as 0.5 μg or less, such as 0.3 μg of exosome is applied to the test animal.

Paragraph 12. Use according to any preceding claim, in which the pharmaceutical composition comprises 40 μg/ml or less, 20 μg/ml or less, 8 μg/ml or less, 4 μg/ml or less, 2 μg/ml or less or 1.2 μg/ml or less of exosome.

Paragraph 13. Use according to any preceding claim, in which the pharmaceutical composition is subcutaneously injected or applied topically.

Paragraph 14. Use according to any preceding claim, in which the percentage of a group of test animals, for example C57BL/6J female mice, to which the pharmaceutical composition is applied which show growth of thick, straight hair is 50% or higher, such as 55% or higher, such as 60% or higher, such as 65% or higher, such as 70% or higher, such as 75% or higher.

Paragraph 15. Use according to Paragraph 14, in which the percentage of a group of control animals to which the pharmaceutical composition is not applied which show growth of thick, straight hair is 40% or lower, such as 35% or lower, such as 30% or lower, such as 25% or lower, such as 20% or lower, such as 15% or lower.

Paragraph 16. Use according to any preceding claim, in which the pharmaceutical composition is capable of enhancing hair growth and wound repair simultaneously.

EXAMPLES

We have previously demonstrated that culture medium conditioned by MSCs derived from human embryonic stem cells or fetal tissues (Lian et al., 2007) (Lai et al., 2010a; Lai et al., 2010b) could protect the heart from injury in a degenerative disease such as myocardial ischemia. Infusion of the CM reduced infarct size in both pig and mouse models of myocardialischemia/reperfusion (MI/R) injury by ~60% and ~50%, respectively (Timmers et al., 2008). Subsequent studies demonstrated that this cardioprotection was mediated by exosomes or microparticles of about 50-100 ηm in diameter and these exosomes carry both protein and RNA load (Chen et al., 2010; Lai et al., 2010a; Lai et al., 2010b; Sze et al., 2007). These exosomes could be purified as a population of homogenously sized particles by size exclusion on HPLC and reduced infarct size in a mouse model of MI/R injury at about a tenth of the dosage of the conditioned medium (Lai et al., 2010a; Lai et al., 2010b). Exosomes are bi-lipid membrane vesicles of 50-100 nm that are secreted by many cell types (reviewed (Thery et al., 2009)). They belong to a class of secreted cellular products known as microparticles which broadly encompasses all secreted membrane vesicles. Other than exosomes, microparticles include microvesicles (100-1000 nm), ectosomes (50-200 nm), membrane particles (50-80 nm), exosome-like vesicles (20-50 nm) and apoptotic vesicles (50-500 nm). The major distinguishing parameter for these different classes of microparticles is their size and the best defined class is the exosomes. Besides their size, exosomes have a density in sucrose of 1.10 to 1.19 g/ml, sedimented at 100,000 g, has a cholesterol-rich lipid membrane containing sphingomyelin, ceramide; lipid rafts; exposed phosphatidylserine. The process of exosome biogenesis is complex and involves complex intracellular membrane traffic through the biosynthetic and endocytotic pathways. As evidence of this complex biogenesis, the hallmark features of exosomes are markers of the endoplasmic reticulum and the endosomes such as Alix, Tsg101, Rab proteins, etc. Exosomes are stored in multivesicular bodies prior to release via fusion of the multivesicular bodies (MVBs) with the plasma membrane.

Here we determine if these MSC exosomes which represent physically distinct subcellular entities containing a defined permutation of proteins and RNAs could enhance wound healing. MSC exosome diluted in saline or saline alone was subcutaneously injected into a mouse model of full thickness wound. The rate of wound closure was enhanced with unexpected enhanced hair growth in the shaved dorsum of exosome-treated mice.

Example 1. Materials and Methods—Preparation of CM

The culture of HuES9.E1 cells and preparation of HuES9.E1 conditioned medium (CM) were performed as described previously (Lian et al., Sze et al., 2007). The CM were concentrated 50× by TFF using a membrane with 100 kDa MWCO (Sartorius, Goettingen, Germany). filtered with a 0.2 um filter before storage or use.

Example 2. Materials and Methods—Purification of Exosomes by HPLC

Exosomes were purified by HPLC as previously described (Lai et al., 2010a). The instrument setup consisted of a liquid chromatography system with a binary pump, an auto injector, a thermostated column oven and a UV-visible detector operated by the Class VP software from Shimadzu Corporation (Kyoto, Japan). The Chromatography columns used were TSK GUARD® column SWXL, 6×40 mm and TSK GEL® G4000 SWX, 7.8×300 mm from Tosoh Corporation (Tokyo, Japan). The following detectors, Dawn 8 (light scattering), Optilab (refractive index) and QELS (dynamic light scattering) were connected in series following the UV-visible detector. The last three detectors were from Wyatt Technology Corporation (California, USA) and were operated by the ASTRA software. The components of the sample were separated by size exclusion i.e. the larger molecules will elute before the smaller molecules. The eluent buffer used was 20 mM phosphate buffer with 150 mM of NaCl at pH 7.2. This buffer was filtered through a pore size of 0.1 µm and degassed for 15 minutes before use. The chromatography system was equilibrated at a flow rate of 0.5 ml/min until the signal in Dawn 8 stabilized at around 0.3 detector voltage units. The UV-visible detector was set at 220 ηm and the column was oven equilibrated to 25° C. The elution mode was isocratic and the run time was 40 minutes. The volume of sample injected ranged from 50 to 100 µl. The % area of the exosome peak vs. all other peaks was integrated from the UV-visible detector. The hydrodynamic radius, $R_h$ was computed by the QELS and Dawn 8 detectors. The highest count rate (Hz) at the peak apex was taken as the $R_h$. Peaks of the separated components visualized at 220 ηm were collected as fractions for further characterization studies.

Example 3. Materials and Methods—Animal Experimentation—Mice

All animal procedures were approved by A*Star's IACUC committee. 8 week old C57BL/6J female mice were used for the study. The animals were anesthetized using inhaled isoflurane (3%) and subcutaneous Avertin (0.3 ml). Following induction of anesthesia, the dorsum of the mice were shaved. A biopsy punch of 177 $mm_2$ (15-mm diameter wound) in diameter was made in the skin. At weekly intervals, CM (3 µg) and exosome (0.3 µg) in 250 µl saline was injected subcutaneously at the wound periphery. The control group received subcutaneous injections of 250 µl saline. In another group, CM or its exosome fraction was mixed with Tisseel glue (Baxter) and applied topically on the wound. Digital photographs of the wound were taken at 48 hour intervals for 14 days.

Example 4. Results—Enhanced Wound Closure—Mice

Figure 2:
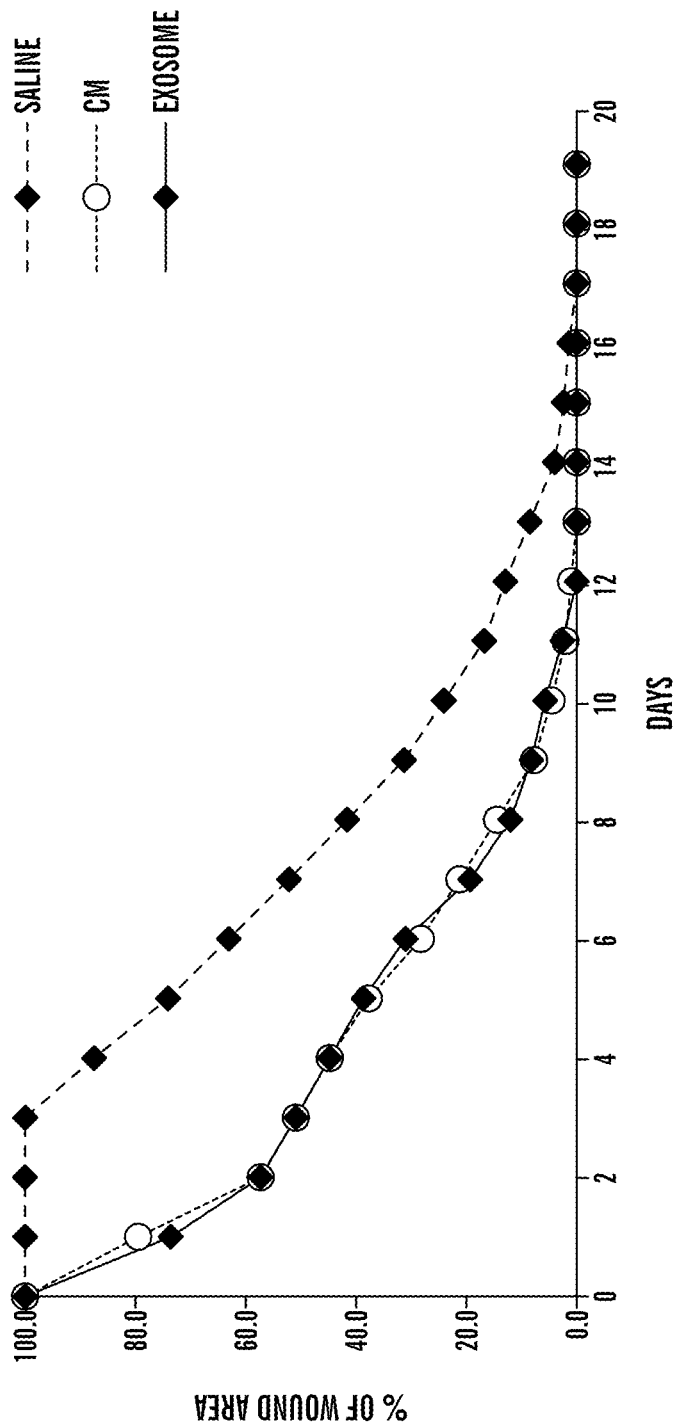
FIG. 2 is a diagram showing a comparison of the rate of wound closure between saline, CM and exosome treatment groups. Based on digital images of the wound taken daily as demonstrated in FIGS. 1A-1B, the wound area in each mouse for each treatment group was measured and normalized against the initial wound area.

The mean time for complete wound closure was 17.0 d in the control group, 13.0 d in the group treated with subcutaneous CM injection (p<0.001). 0.3 µg CM-derived exosome enhanced wound closure to the same extent as 3 µg CM i.e. 12.3 d vs 13.0 d, respectively (p=0.99) (FIG. 1). Mice treated with saline had a lag phase of 3 days prior to commencement of wound healing while this lag phase was absent in mice treated with either CM or exosome (FIG. 2).

The mean wound closure time for mice treated with CM mixed with Tisseel glue was 14.6 d vs 13.0 d for those treated with subcutaneous perilesional CM injections (t test, p=0.48). Although this difference was not statistically significant due possibly to the small sample size, this difference may reflect some loss of the therapeutic agent during topical application as opposed to injection.

Example 5. Results—Enhanced Hair Growth—Mice

Mice treated with CM or exosome showed significant re-growth of hair with 15 of 20 mice (75%) showed growth of thick, straight hair similar to the unshaved hair, while 8 mice (40%) in the control group showed very sparse regrowth of hair (FIG. 1).

Example 6. Materials and Methods—Animal Experimentation—Pigs

Minipigs were fasted from the night prior to surgery. Each pig was housed in a single cage. The pigs were anesthetized with a mixture of Zoletil (6 mg/kg) and Xylazine (0.5 mg/kg).

The dorsum of the animals were shaved and skin antisepsis performed with iodine or chlorhexidine scrub followed by alcohol wipe. A final alcohol wipe/spray was done after transfer into the operating room, just before draping.

Forty full thickness skin wound of 17-mm diameters were made in the dorsum of the minipigs. The mean distance between each wound was 3 cm.

Each wound was injected at four sites with a total volume of 200 µl of one of the following: saline, conditioned medium from huES9.E1 MSCs, exosome from huES9.E1 MSCs (0.3 µg per 200 µl) or exosome from myc-transformed huES9.E1 MSCs (0.3 µg per 200 µl) with an average of 4 injections per wound.

The injection was carried out every 2 or 3 days.

Wound size was measured with a caliper/ruler every 48 hours and imaged with a digital camera.

Example 7. Enhanced Hair Growth and Wound Closure—Pigs

Figure 3:
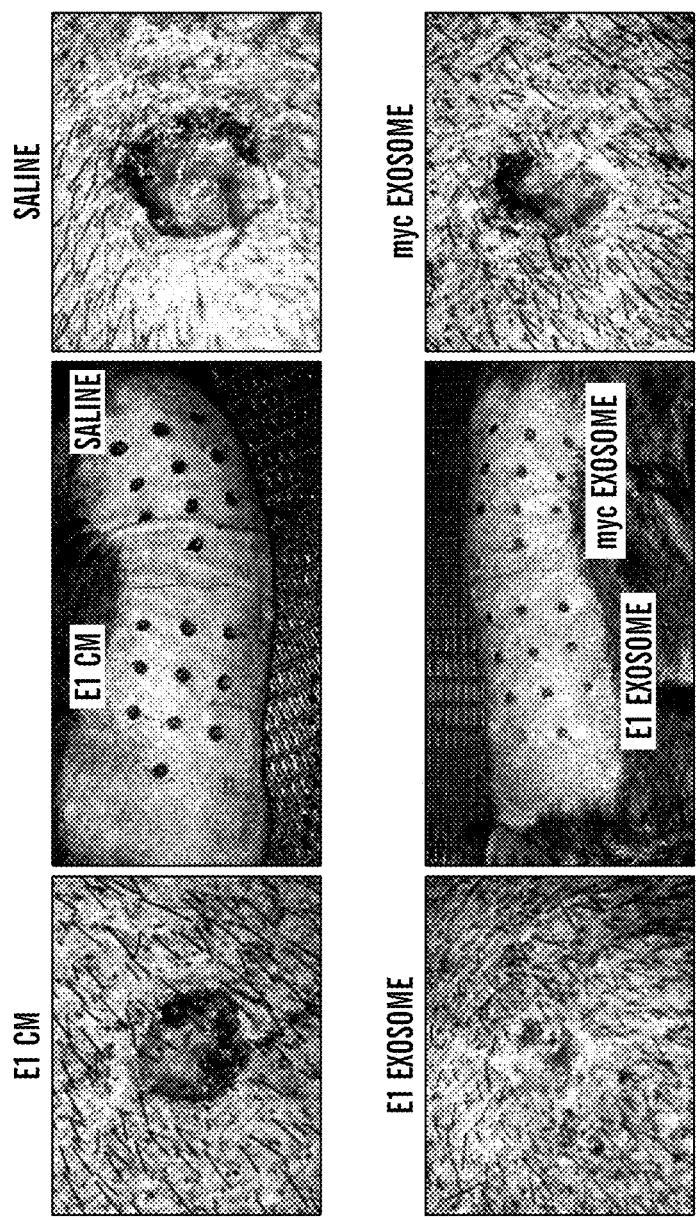
FIG. 3 is a diagram showing enhanced wound closure and hair growth of pigs. Middle column: dorsum of pig divided into four quadrants with 10 wounds per quadrant. The wounds in the right upper quadrant were treated with conditioned medium from huES9.E1 MSCs (E1.CM), the right lower quadrant with saline, the left upper quadrant with exosome from huES9.E1 MSCs (E1 exosome) and the left lower quadrant with exosome from myc-transformed huES9.E1 MSCs (myc exosome). Left and right columns: representative wounds from each of the quadrant two weeks after wounding of the skin. The scab from the wounds were removed and photographed. Conditioned medium or exosome-treated wounds showed increased epithelial coverage and hair growth (arrows).

FIG. 3 shows the results of enhanced hair growth and enhanced wound closure with treatment using exosomes.

In the middle top and bottom panels of FIG. 3, the dorsum of the pig was divided into four quadrants with ten wounds per quadrant. The wounds in the right upper quadrant were treated with conditioned medium from huES9.E1 MSCs (E1.CM), the right lower quadrant with saline, the left upper quadrant with exosome from huES9.E1 MSCs (E1 exosome) and the left lower quadrant with exosome from myc-transformed huES9.E1 MSCs (myc exosome).

In the panels on either the left or right are representative wounds from each of the quadrant two weeks after wounding of the skin. The scab from the wounds was removed and photographed.

Conditioned medium or exosome-treated wounds showed increased epithelial coverage and hair growth (arrows).

Example 8. Enhanced Wound Closure—Human Skin

Wounding in human skin samples and its subsequent culture were performed as previously described (Ref: Eplasty. 2009; 9: e5; Open Rheumatol J. 2008; 2: 17-22; Toxicol Pathol August 2007 vol. 35 no. 5 693-701).

Briefly, human skin samples were trimmed before a centre core that included the epidermis and the upper dermis was removed. Every day, the culture medium was changed, 20 µl exosome (0.1 µl/ml) or phosphate buffered saline was injected into the edge of each central core wound and a digital image of each skin sample was captured.

Figure 4:
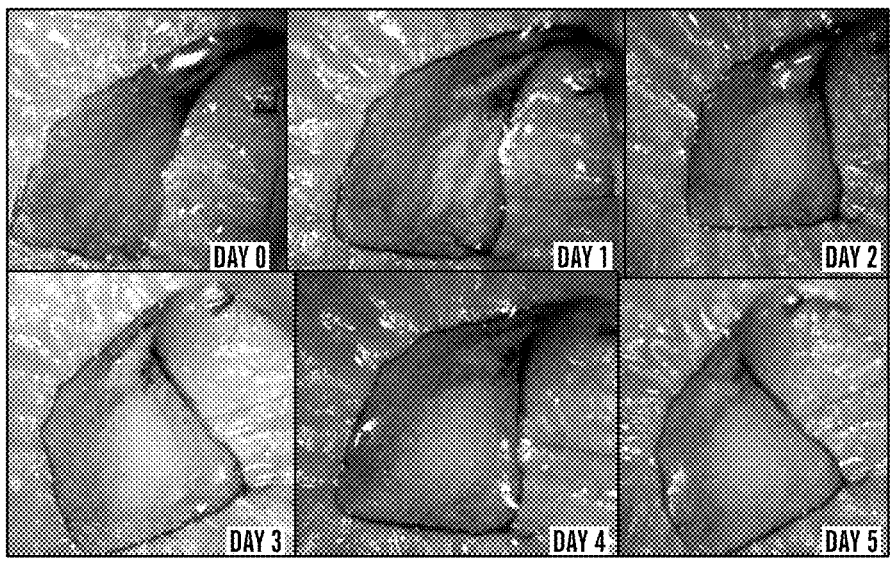
FIG. 4 is a diagram showing enhanced wound closure on human skin. Skin samples at different days after treatment with PBS (top) and exosomes (bottom) were stained with a supravital dye, hematoxylin. Digital images were taken.
Figure 4:
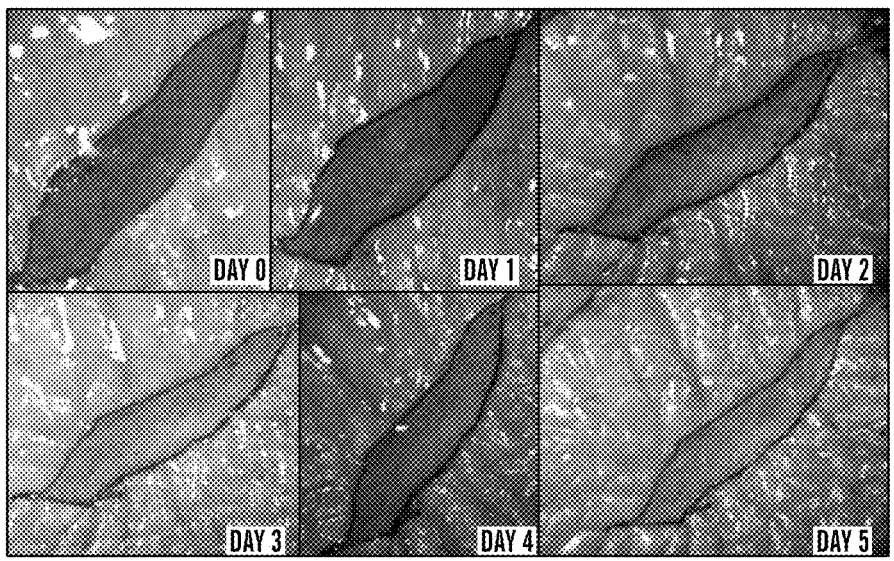
Figure 5:
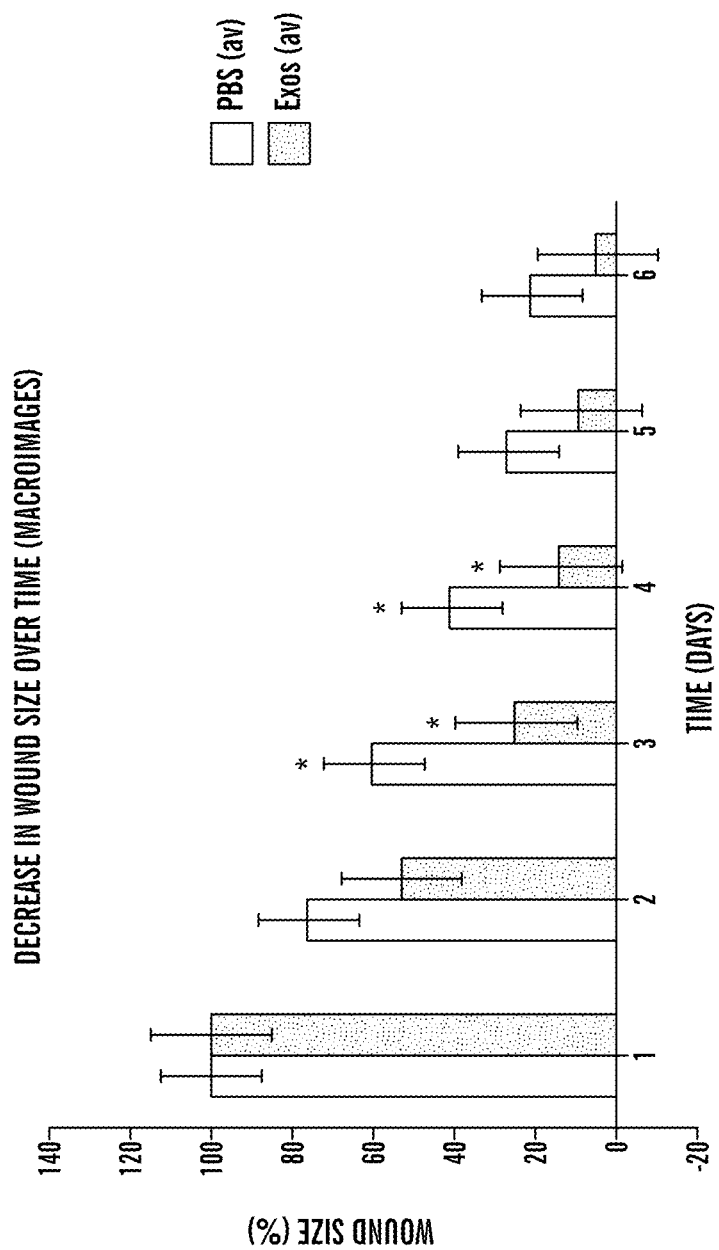
FIG. 5 is a diagram showing enhanced wound closure on human skin. Wound area of each skin sample treated with PBS (white bars) and exosomes (gray bars) as determined in FIG. 4 above was plotted against time. The wound size for each sample at day 1 was normalized to 100%.

As shown in FIG. 4 and FIG. 5, wound closure was significantly faster at day 3 and day 4 of treatment. Exosomes therefore increased wound closure in human skin culture.

Example 9. Discussion

Mesenchymal stem cells from different tissue sources have been shown to enhance wound healing (reviewed (Cha and Falanga, 2007)). While some studies have demonstrated that MSCs enhance wound healing by differentiating and replacing damaged cells or tissues such as blood vessels (Wu et al., 2007a), sweat gland cells (Li et al., 2006) or multiple cell types in the skin such as vascular endothelial cells, sebaceous duct cells, and epidermal cells (Fu et al., 2006; Sasaki et al., 2008), it is increasingly reported that MSC mediates wound healing through its secretion (Chen et al., 2008; Kim et al., 2009; Kim et al., 2007; Yoon et al., 2009).

We recently demonstrated that exosomes secreted by human ESC-derived MSCs were cardioprotective at one-tenth dosage of culture medium conditioned by these MSCs, indicating that exosomes are the active protective elements in the secretion (Lai et al., 2010a; Lai et al., 2010b). Unlike previous reports on the paracrine secretion of MSC which focus on small secretory molecules such as chemokines and cytokines, exosomes are large particles of about 50-100 m and contain proteins and RNAs that are generally cytoplasmic or membrane-bound, and are not known to be secreted. Consistent with their role as the active protective agent in MSC secretion, these purified exosomes also mediated wound closure and unexpectedly enhanced hair growth. The extent of enhanced wound closure and hair growth at 0.3 µg exosome per mouse was similar to that in mice treated with 3 µg CM per mouse, confirming that exosome was the active protective agent in the CM.

REFERENCES

Abdallah, B. M., and Kassem, M. (2009). The use of mesenchymal (skeletal) stem cells for treatment of degenerative diseases: Current status and future perspectives. Journal of Cellular Physiology 218, 9 12.

Arthur, A., Zannettino, A., and Gronthos, S. (2009). The therapeutic applications of multipotential mesenchymal/stromal stem cells in skeletal tissue repair. J Cell Physiol 218, 237 245.

Baer, P. C., and Geiger, H. (2010). Mesenchymal stem cell interactions with growth factors on kidney repair. Curr Opin Nephrol Hypertens 19, 1 6.

Caplan, A. I., and Dennis, J. E. (2006). Mesenchymal stem cells as trophic mediators. J Cell Biochem 98, 1076 1084.

Cha, J., and Falanga, V. (2007). Stem cells in cutaneous wound healing. Clin Dermatol 25, 73 78.

Chen, L., Tredget, E. E., Wu, P. Y., and Wu, Y. (2008). Paracrine factors of mesenchymal stem cells recruit macrophages and endothelial lineage cells and enhance wound healing. PLoS ONE 3, e1886.

Chen, T. S., Lai, R. C., Lee, M. M., Choo, A. B., Lee, C. N., and Lim, S. K. (2010). Mesenchymal stem cell secretes microparticles enriched in pre microRNAs. Nucleic Acids Res 38, 215 224.

Fu, X., Fang, L., Li, X., Cheng, B., and Sheng, Z. (2006). Enhanced wound healing quality with bone marrow mesenchymal stem cells autografting after skin injury. Wound Repair Regen 14, 325 335.

Giordano, A., Galderisi, U., and Marino, I. R. (2007). From the laboratory bench to the patient's bedside: an update on clinical trials with mesenchymal stem cells. J Cell Physiol 211, 27 35.

Granero Molto, F., Weis, J. A., Longobardi, L., and Spagnoli, A. (2008). Role of mesenchymal stem cells in regenerative medicine: application to bone and cartilage repair. Expert Opin Biol Ther 8, 255 268.

Kim, W. S., Park, B. S., and Sung, J. H. (2009). Protective role of adipose derived stem cells and their soluble factors in photoaging. Arch Dermatol Res 301, 329 336.

Kim, W. S., Park, B. S., Sung, J. H., Yang, J. M., Park, S. B., Kwak, S. J., and Park, J. S. (2007). Wound healing effect of adipose derived stem cells: a critical role of secretory factors on human dermal fibroblasts. J Dermatol Sci 48, 15 24.

Lai, R. C., Arslan, F., Lee, M. M., Sze, N. S., Choo, A., Chen, T. S., Salto Tellez, M., Timmers, L., Lee, C. N., El Oakley, R. M., et al. (2010a). Exosome secreted by MSC reduces myocardial ischemia/reperfusion injury. Stem Cell Res.

Lai, R. C., Arslan, F., Tan, S. S., Tan, B., Choo, A., Lee, M. M., Chen, T. S., Teh, B. J., Eng, J. K., Sidik, H., et al. (2010b). Derivation and characterization of human fetal MSCs: An alternative cell source for large scale production of cardioprotective microparticles. J Mol Cell Cardiol.

Li, H., Fu, X., Ouyang, Y., Cai, C., Wang, J., and Sun, T. (2006). Adult bone marrow derived mesenchymal stem cells contribute to wound healing of skin appendages. Cell Tissue Res 326, 725 736.

Lian, Q., Lye, E., Suan Yeo, K., Khia Way Tan, E., Salto Tellez, M., Liu, T. M., Palanisamy, N., El Oakley, R. M., Lee, E. H., Lim, B., et al. (2007). Derivation of Clinically Compliant MSCs from CD105+, CD24 Differentiated Human ESCs. Stem Cells 25, 425 436.

Phinney, D. G., and Prockop, D. J. (2007). Concise Review: Mesenchymal Stem/Multipotent Stromal Cells: The State of Transdifferentiation and Modes of Tissue Repair Current Views. Stem Cells 25, 2896 2902.

Sadan, O., Melamed, E., and Offen, D. (2009). Bone marrow derived mesenchymal stem cell therapy for neurodegenerative diseases. Expert Opin Biol Ther 9, 1487 1497.

Sasaki, M., Abe, R., Fujita, Y., Ando, S., Inokuma, D., and Shimizu, H. (2008). Mesenchymal stem cells are recruited into wounded skin and contribute to wound repair by transdifferentiation into multiple skin cell type. J Immunol 180, 2581 2587.

Spitkovsky, D., and Hescheler, J. (2008). Adult mesenchymal stromal stem cells for therapeutic applications. Minim Invasive Ther Allied Technol 17, 79 90.

Sze, S. K., de Kleijn, D. P., Lai, R. C., Khia Way Tan, E., Zhao, H., Yeo, K. S., Low, T. Y., Lian, Q., Lee, C. N., Mitchell, W., et al. (2007). Elucidating the secretion proteome of human embryonic stem cell derived mesenchymal stem cells. Mol Cell Proteomics 6, 1680 1689.

Thery, C., Ostrowski, M., and Segura, E. (2009). Membrane vesicles as conveyors of immune responses. Nat Rev Immunol 9, 581 593.

Timmers, L., Lim, S. K., Arslan, F., Armstrong, J. S., Hoefler, I. E., Doevendans, P. A., Piek, J. J., El Oakley, R. M., Choo, A., Lee, C. N., et al. (2008). Reduction of myocardial infarct size by human mesenchymal stem cell conditioned medium. Stem Cell Research 1, 129 137.

Wu, Y., Chen, L., Scott, P. G., and Tredget, E. E. (2007a). Mesenchymal stem cells enhance wound healing through differentiation and angiogenesis. Stem Cells 25, 2648 2659.

Wu, Y., Wang, J., Scott, P. G., and Tredget, E. E. (2007b). Bone marrow derived stem cells in wound healing: a review. Wound Repair Regen 15 Suppl 1, S18 26.

Yoon, B. S., Moon, J. H., Jun, E. K., Kim, J., Maeng, I., Kim, J. S., Lee, J. H., Baik, C. S., Kim, A., Cho, K. S., et al.

(2009). Secretory Profiles and Wound Healing Effects of Human Amniotic Fluid derived Mesenchymal Stem Cells. Stem Cells Dev.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

We claim:

1. A method of promoting or enhancing healing of a full-thickness skin wound, the method consisting essentially of: topically administering to a human subject in need thereof a pharmaceutical composition comprising a therapeutically effective amount of human mesenchymal stem cell exosomes to the full-thickness skin wound wherein the full-thickness skin wound is at least 15 mm in diameter, and,
    wherein the therapeutically effective amount of human mesenchymal stem cell exosomes is at least an amount effective to reduce the time taken for complete excisional wound closure by at least 10% when administered as a single dose to a circular, 15 millimeter diameter, excisional skin wound on a mouse, compared to the time taken for complete wound closure on a mouse not administered the human mesenchymal stem cell exosomes.

2. The method of claim 1, wherein the pharmaceutical composition comprises 40 µg/ml or less of the human mesenchymal stem cell exosomes.

3. The method of claim 1, wherein the human mesenchymal stem cell exosomes:
    (a) have a size between 50 nm and 100 nm as determined by electron microscopy;
    (b) comprise a complex of molecular weight >100 kDa comprising proteins of <100 kDa;
    (c) comprises a complex of molecular weight >300 kDa comprising proteins of <300 kDa;
    (d) comprises a complex of molecular weight >1000 kDa;
    (e) have a size of between 2 nm and 200 nm as determined by filtration against a 0.2 µM filter and concentration against a membrane with a molecular weight cut-off of 10 kDa; or
    (f) have a hydrodynamic radius below 100 nm as determined by laser diffraction or dynamic light scattering.

4. The method of claim 3, wherein the human mesenchymal stem cell exosomes have a size between 50 and 100 nm.

5. The method of claim 3, wherein the human mesenchymal stem cell exosomes have a hydrodynamic radius between about 45 and about 55 nm.

6. The method of claim 1, wherein the full-thickness skin wound is a decubitus ulcer.

7. The method of claim 1, wherein the full-thickness skin wound is a burn.

8. The method of claim 1, wherein the effective amount of human mesenchymal stem cell exosomes promotes re-epithelialization of the full-thickness skin wound.

9. The method of claim 1, wherein the wound is a chronic wound.

* * * * *